US012072336B2

(12) United States Patent
Tajbakhsh et al.

(10) Patent No.: US 12,072,336 B2
(45) Date of Patent: Aug. 27, 2024

(54) METHODS FOR SINGLE-CELL PROSTATE TISSUE CLASSIFICATION AND PREDICTION OF CANCER PROGRESSION

(71) Applicants: CEDARS-SINAI MEDICAL CENTER, Los Angeles, CA (US); TRUSTEES OF THE UNIVERSITY OF PENNSYLVANIA, Philadelphia, PA (US)

(72) Inventors: Jian Tajbakhsh, Encino, CA (US); Darko Stefanovski, West Chester, PA (US)

(73) Assignees: Cedars-Sinai Medical Center, Los Angeles, CA (US); Trustees of The University of Pennsylvania, Philadelphia, PA (US)

( * ) Notice: Subject to any disclaimer, the term of this patent is extended or adjusted under 35 U.S.C. 154(b) by 866 days.

(21) Appl. No.: 16/342,297

(22) PCT Filed: Oct. 20, 2017

(86) PCT No.: PCT/US2017/057557
§ 371 (c)(1),
(2) Date: Apr. 16, 2019

(87) PCT Pub. No.: WO2018/075873
PCT Pub. Date: Apr. 26, 2018

(65) Prior Publication Data
US 2020/0057069 A1 Feb. 20, 2020

Related U.S. Application Data

(60) Provisional application No. 62/410,689, filed on Oct. 20, 2016.

(51) Int. Cl.
*G01N 33/574* (2006.01)
*C12Q 1/6804* (2018.01)
*G01N 1/30* (2006.01)
*G01N 21/64* (2006.01)

(52) U.S. Cl.
CPC ..... *G01N 33/57434* (2013.01); *C12Q 1/6804* (2013.01); *G01N 1/30* (2013.01); *G01N 21/6428* (2013.01); *G01N 21/6447* (2013.01); *G01N 21/6458* (2013.01); *G01N 2001/302* (2013.01); *G01N 2021/6439* (2013.01); *G01N 2201/12* (2013.01)

(58) Field of Classification Search
CPC ........... G01N 33/57434; G01N 33/574; C12Q 1/68; C12Q 2600/154
See application file for complete search history.

(56) References Cited

U.S. PATENT DOCUMENTS

| 2011/0300490 A1* | 12/2011 | Rachet | G02B 26/0833 |
| | | | 359/385 |
| 2014/0371082 A1* | 12/2014 | Conti | C12Q 1/6806 |
| | | | 435/6.1 |
| 2017/0211153 A1* | 7/2017 | Kohli | C12Q 1/6886 |

FOREIGN PATENT DOCUMENTS

| WO | 2014082096 A1 | 5/2014 |
| WO | 2014159443 A1 | 10/2014 |
| WO | 2016033542 A1 | 3/2016 |
| WO | 2016172612 A1 | 10/2016 |
| WO | 2018075873 A1 | 4/2018 |

OTHER PUBLICATIONS

Brothman et al., Cancer Genetics and Cytogenetics 156 :31-36 (Year: 2005).*
Dikaios et al., Eur. Radiol. 25 :2727-2737 (Year: 2015).*
Ferrer-Roca et al., Computer Assisted Microscopy. Proceedings of the 3rd Intl. Conf. on Bio-Inspired Systems and Signal Processing pp. 517-522 (Year: 2010).*
Forsslund et al., Cancer 69:1432-1439 (Year: 1992).*
Haffner et al., Oncoyyyytarget 2(8) :627-637 (Year: 2011).*
Isharawal et al., Urology 77: 763.e1-763.e6 (Year: 2011).*
Jiang el., PLOS one 8(10) : e74386 (Year: 2013).*
Kerr et al., Chromosome Res 18 :677-688 (Year: 2010).*
Kunju et al., Histopathology 47 :587-596 (Year: 2005).*
Otto, F.J. Methods in Cell Biology41:211-217 (Year: 1994) Copy upon request via e-mail.*
Paris et al., The Prostate 67:1447-1455 (Year: 2007).*
Peng et al., Prostate Cancer and Prostatic Disease 17: 81-90 (Year: 2014).*
Shankey et al. Cytometry 14:497-500 (Year: 1993).*
Stephenson et al., Cancer Research 47: 2504-2509 (Year: 1987).*
Strand et al., Clinical Epigenetics 7:111 (Year: 2015).*
Veltri et al., J. of Cellular Biochemistry, Suppl. 19 :249-258 (Year: 1994).*
Yang et al.,Nucleic Acids Research 32(3) : e38 (Year: 2004).*
Yegnasubramanian et al., Cancer Reseach 68(21) :8954 (Year: 2008).*
Zelic et al., Prostate Cancer and Prostatic Disease 18:1-12 (Year: 2015).*
Otto, F.J. "Methods in Cell Biology" 41 : 211-217 (Year: 1994).*
Adolfsson, J., Intl. Journal of Cancer 58:211-216 (Year: 1994).*
Trewarthhha et al., Nature Reviews | Drug Discovery 12: 823-824 (Year: 2013).*
Wallis et al., European Urology 70: 21-30 (epub 2015) (Year: 2016).*

(Continued)

*Primary Examiner* — Ethan C Whisenant
(74) *Attorney, Agent, or Firm* — Nixon Peabody LLP

(57) ABSTRACT

In certain embodiments, this application discloses methods for the diagnosis and prognosis of prostate cancer. In some embodiments, the invention takes advantage of the combinatorial utility of certain biomarkers to prognose and diagnose prostate cancer at an early stage. In certain embodiments, the methods described herein do not require the selection of cells from a particular tissue compartment, and are therefore suitable for analysis of cancer tissue in which compartmentalization is lost.

15 Claims, 12 Drawing Sheets

(56) References Cited

OTHER PUBLICATIONS

International Search Report and Written Opinion for PCT/US2017/057557 dated Jan. 10, 2018, 21 pages.
Bouazza et al., Gene-Expression-Based Cancer Classification Through Feature Selection with KNN and SVM Classifiers, Intelligent Systems and Computer Vision, 2015, pp. 1-6.
Chandana wt al., Staging of Prostate Cancer Using Automatic Feature Selection, Sampling and Dempster-Shafer Fusion, Cancer Informatics, 2009, vol. 7, pp. 57-73.
Gertych et al., 3-D DNA Methylation Penotypes Correlate with Cytotoxicity Levels in Prostate and Liver Cancer Cell Models, BMC Pharmacology and Toxicology, 2013, vol. 14(11), pp. 1-21.
Leica Microsystems, Leica TCS SP5 X User Manual, Product Manual, Retrieved from: http://www.zmbh.uni-heidelberg.de/Central_services/Imaging_Facility/info/SP5.pdf on Dec. 11, 2017, 99 pages.
Moore et al., The Use of Multiple Novel Tumor Biomarkers for the Detection of Ovarian Carcinoma in Patients with Pelvic Mass, Gynecologic Oncology, 2008, vol. 108(2), pp. 402-408.
Polat et al., Histologic Evaluation in Patients With Benign Prostatic Hyperplasia Treated with Finasteride and Surgery Alone, Turkish Journal of Medical Sciences, 1998, vol. 28, pp. 157-161.
Stefanovski et al., Prostate Cancer Diagnosis Using Epigenetic Biomarkers, 3D High-Content Imaging and Probabilistic Cell-By-Cell Classifiers, Oncotarget, 2017, vol. 8(34), pp. 57278-57301.
Tajbakhsh et al., Dynamic Heterogeneity of DNA Methlation and Hydroxymethylation in Embryonic Stem Cell Populations Captured by Single-Cell 3D High-Content Analysis, Experimental Cell Research, 2015, vol. 332(2), pp. 190-201.
Zha et al., Alpha-Methylacyl-CoA Racemase as an Androgen-Independent Growth Modifier in Prostate Cancer, Cancer Research, 2003, vol. 63, pp. 7365-7376.

* cited by examiner

METHODS FOR SINGLE-CELL PROSTATE TISSUE CLASSIFICATION AND PREDICTION OF CANCER PROGRESSION

CROSS-REFERENCE TO RELATED APPLICATIONS

This application is the national phase of International Application No. PCT/US2017/057557, filed Oct. 20, 2017, which designated the U.S. and that International Application was published under PCT Article 21(2) in English. This application claims priority under 35 U.S.C. § 119(e) to U.S. Provisional Patent Application No. 62/410,689, filed Oct. 20, 2016, the contents of which are herein incorporated by reference in its entirety.

STATEMENT REGARDING FEDERALLY SPONSORED RESEARCH OF DEVELOPMENT

This invention was made with government support under Grant No. W81XWH-10-1-0939 awarded by the Department of Defense. The government has certain rights in the invention.

FIELD OF THE INVENTION

The present invention generally relates to the diagnosis, prognosis, and treatment of cancer, and especially prostate cancer (PCa).

BACKGROUND

The following description includes information that may be useful in understanding the present invention. It is not an admission that any of the information provided herein is prior art, or relevant to the presently claimed invention.

Assessment of needle core biopsy at diagnosis and larger biopsies at prostatectomy are standard care for prostate cancer screening and therapeutic strategy. The problem in prostate cancer diagnosis and prognosis is that histopathological assessment of tissue biopsies is still performed using mainly morphological parameters. However, in prostate tissue, in tumor regions as well as the tumor environment, cells may have undergone aberrant (cancerous) changes based on molecular properties (genetics, epigenetics) that do not necessarily affect cell and tissue morphology and thus can become undetected using current pathological practices. If needle biopsy misses severely changed morphology in parts of the tumor, diagnosis often results in false-negative calls. There is clearly a need in the art for improved methods for prostate cancer diagnosis and prognosis.

BRIEF DESCRIPTION OF THE DRAWINGS

Exemplary embodiments are illustrated in the referenced figures. It is intended that the embodiments and figures disclosed herein are to be considered illustrative rather than restrictive.

FIGS. 8A-8D depicts in accordance with various embodiments of the invention, sample prostate tissue staining. (A) H&E stained needle biopsy 2 of Patient 1 showing adenocarcinoma imaged using an automated scanner (Aperio ScanScope AT turbo, Leica Biosystems) with a 20xNA0.7 lens. Tumor compartments can be easily identified on the aerial (whole) image. (B) A tumor subregion (circle in FIG.

2A) was 10× zoomed in to identify tumor areas for fluorescence confocal imaging and the analysis of these areas in consecutive tissue sections that were labeled by immunofluorescence. (C) Confocal dual-color image (mid-section) of the same subregion at 40× magnification (imaged with a TCS SP5 X Supercontinuum microscope, Leica Microsystems); cell nuclei are delineated by DAPI (false-colored blue) and tumor regions highlighted by cytoplasmic AMACR (cyan). Needle biopsies were completely imaged, whereas larger tissues derived from prostatectomies were imaged using the abovementioned strategy.

Figure 9:
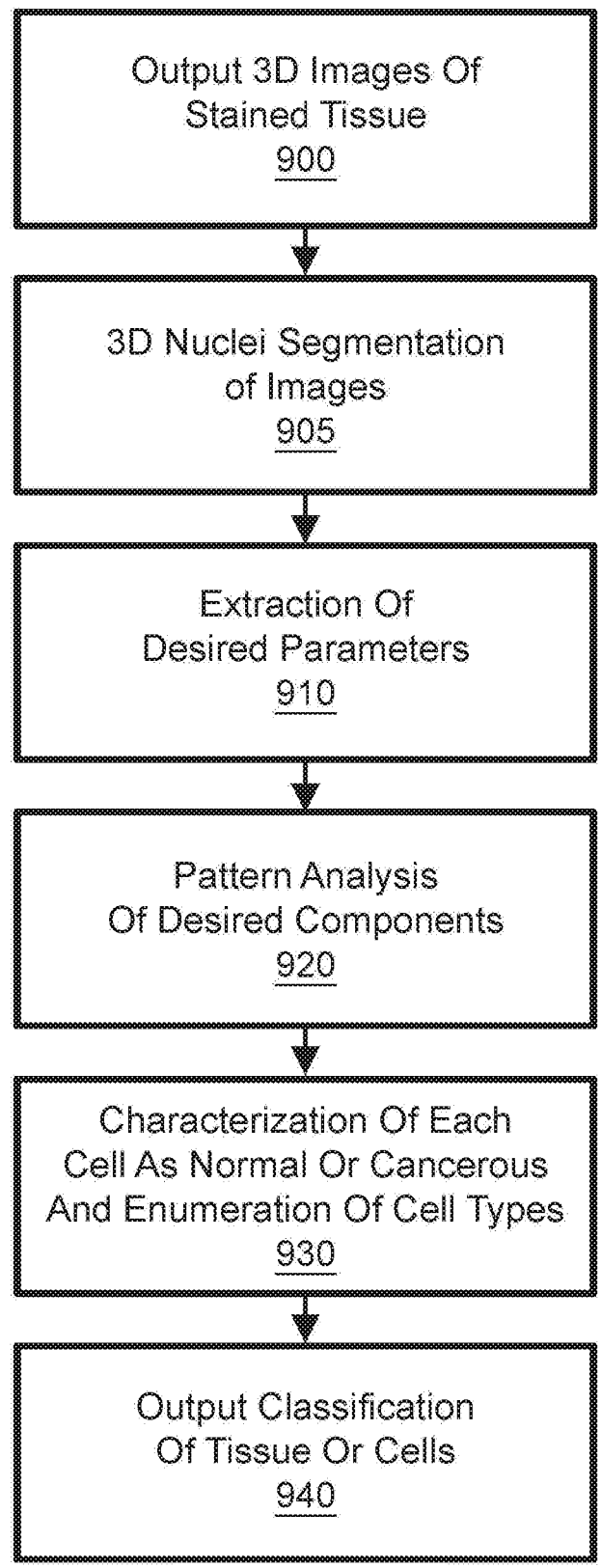

FIG. 9, depicts in accordance with various embodiments of the invention, a flow chart showing an example method for analyzing 3D images and extracted data.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, NY 2006); Smith, *March's Advanced Organic Chemistry Reactions, Mechanisms and Structure* 7$^{th}$ ed., J. Wiley & Sons (New York, NY 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, NY 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor NY, 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U. S. Pat, No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

"Conditions" and "disease conditions," as used herein, may include but are in no way limited to those conditions that are associated with cancer or pre-cancer, including, but in no way limited to prostate cancer.

"Mammal," as used herein, refers to any member of the class Mammalia, including, without limitation, humans and nonhuman primates such as chimpanzees and other apes and monkey species; farm animals such as cattle, sheep, pigs, goats and horses; domesticated mammals, such as dogs and cats; laboratory animals including rodents such as mice, rats and guinea pigs, and the like. The term does not denote a particular age or sex. Thus, adult and newborn subjects, whether male or female, are intended to be included within the scope of this term. While cancer or pre-cancer can be detected in humans according to the inventive methods described herein, detecting cancer in any mammal according to the inventive methods is within the scope of the invention.

The terms "global 5mC" and "5mC content" are used herein interchangeably, and in each case can be defined as the total amount of 5-methylcytosine molecules present in a cell nucleus.

The terms "global 5hmC" and "5hmC content" are used herein interchangeably, and in each case can be defined as the total amount of 5-hydroxymethylcytosine molecules present in a cell nucleus. The term "global DNA (gDNA)" as used herein means the total amount of DNA present in a cell nucleus.

By way of additional background, prostate cancer (PCa) diagnosis/prognosis and patient stratification can benefit from novel concepts and biomarkers that can distinguish between patients who need immediate therapy (progressive cancer) from those who should be rather monitored (indolent cancer). Also, standard histopathology of biopsied tissue still suffers from a 20-30% risk of false-negative diagnosis of PCa. As described in the examples set forth herein, the inventors explored the potential of selected epigenetic markers in combination with validated histopathological markers, 3D high-content imaging, single-cell analysis, and developed mathematical-statistical learning methods a) in generating novel detailed maps of biomarker heterogeneity in patient tissues, and b) in PCa diagnosis and prognosis. Tissues from biopsies and radical prostatectomies from 5 patients were used for building a repertoire of around 140,000 analyzed cells across all tissue compartments and for subsequent model development; and from 5 patients together with the two well-characterized HPrEpiC primary and LNCaP cancer cell types for model validation. Principal component analysis resulted in highest covariability for the four biomarkers 4',6-diamidino-2-phenylindole (DAPI), 5-methylcytosine, 5-hydroxymethylcytosine, and alpha-methylacyl-CoA racemase in the epithelial compartment of tissues. The panel also showed excellent performance in discriminating between normal and cancer-like cells in human prostate tissues; with a sensitivity and specificity of 85%. The panel could correctly classify 87% of HPrEpiC as healthy cells, and 99% of the LNCaP cells as cancer-like. The panel was also able to identify a majority of aberrant cells within histopathologically benign tissues taken at first diagnosis (patients were later diagnosed with adenocarcinoma). Using k-nearest neighbor classifier with cells from an initial patient biopsy, the biomarker panel was able to predict cancer stage and grade of prostatic tissue that occurred at later prostatectomy with 79% accuracy.

With the foregoing background in mind, certain specific non-limiting embodiments are described below.

In various embodiments, the invention teaches a method for determining if one or more prostate cells of a prostate tissue sample are cancerous (aberrant) or noncancerous (benign). In some embodiments, the method includes quantifying one or more, two or more, three or more, or four or more biomarkers in the one or more prostate cells. In some embodiments, the biomarkers comprise, consist of, or consist essentially of one or more of global DNA (gDNA), 5-methylcytosine (5mC), 5-hydroxymethlcytosine (5hmC), and alpha-methylacyl-CoA racemase (AMACR). In some embodiments, all of the aforementioned biomarkers are quantified. In certain embodiments, the method further includes determining if one or more of the prostate cells are cancerous or non-cancerous, based on the quantity of one or more of the biomarkers relative to cancerous and/or non-cancerous cells, wherein a significantly higher quantity of gDNA and/or AMACR and/or a significantly lower quantity of 5mC and/or 5hmC, relative to non-cancerous cells, is indicative of prostate cancer. In some embodiments, the method further includes utilizing a logistic regression model (e.g., as described herein in greater detail in the "Examples" section of the present application) to predict a composition of aberrant versus benign cells in the prostate tissue sample. In other words, in some embodiments the purpose of the logistic regression as applied in the inventive methods is to categorize individual cells within a tissue and determine whether each of them is benign (normal) or cancerous (aberrant). Then determine whether tissue is benign or malignant, based on cell composition. In some embodiments, the method includes utilizing a k-nearest neighbor (KNN) classification to (1) correlate the prostate tissue cell composition with cancer staging and/or grading of cancer progression, and (2) predict how tissue stage and grade would be upon subsequent prostatectomy. Thus, in some embodiments the inventive methods can be used to determine PCa/tissue indolence or progressiveness (i.e., cancer progressiveness). In other words, the inventive methods can be used for determining a prognosis for a patient. In certain embodiments, the cancer stage and/or pathological category is defined as any type of cancer stage and/or pathological categories known in the art, including, but in no way limited to any cancer stage and/or pathological category described in the specific examples set forth herein. The cancer stages and/or pathological categories and types of staging and/or pathological categorization represented in the examples specifically set forth herein are in no way meant to limit the scope of the present invention. Other cancer stages and/or pathological categories are well known in the art. For instance, stage I and stage IV. Further, there is the TNM classification used for tumors that lead to other types of tumor descriptions such as prostatic intraepithelial neoplasias (PINs), inarticulate carcinoma, basal cell carcinoma, intraductal carcinoma etc. Additionally, other GS <6 and GS >7 exist that are not described in the experiments and discussion of the "Examples" section. This is because the specific examples provided in the present application focus only on the current grey zone of the PCa-field, which is stages II and III, and GS6 and GS7, where it is especially difficult to make decisions regarding cancer treatment and patient stratification.

In various embodiments described above, the prostate tissue is obtained from a biopsy. In some embodiments, rather than prostate tissue, a liquid biopsy containing one or more cells is obtained in the form of urine, blood, semen, or combinations thereof.

In certain embodiments, the quantity of 5mC in one or more of the prostate cells is determined by high-resolution light microscopy in conjunction with computer-assisted image analysis after one or more of the prostate cells have been subjected to immunofluorescence staining with an antibody specific for 5mC. In some embodiments, the quantity of 5hmC in one or more of the prostate cells is determined by high-resolution light microscopy in conjunction with computer-assisted image analysis after one or more of the prostate cells have been subjected to immunofluorescence staining with an antibody specific for 5hmC. In some embodiments, the quantity of AMACR in one or more of the prostate cells is determined by high-resolution light microscopy in conjunction with computer-assisted image analysis after one or more of the prostate cells have been subjected to immunofluorescence staining with an antibody specific for AMACR. In certain embodiments, the quantity of gDNA in one or more of the prostate cells is determined by high-resolution light microscopy in conjunction with computer-assisted image analysis after one or more of the prostate cells have been treated with DAPI. In some embodiments, one or more of the biomarkers are quantified by high-resolution light microscopy in conjunction with computer-assisted image analysis, as described herein or referenced in the "Examples" section. In certain embodiments, the microscope is a confocal scanning microscope with a resolution equal to or less than one micrometer.

In various embodiments, any commercially available monoclonal or polyclonal antibody specific for 5mC could be utilized in conjunction with the inventive methods described herein. For example, the 5mC antibody could be obtained from vendors such as Aviva Systems Biology, Corp. (San Diego, CA), GeneTex, Inc. (Irvine, CA), Active Motif, Inc. (Carslbad, CA), and Diagenode, Inc. (Denville, NJ) to name a few. In some embodiments, the 5mC antibody is the antibody described in Reynaud C., et al. Monitoring of urinary excretion of modified nucleosides in cancer patients using a set of six monoclonal antibodies. Cancer Lett 1992 Mar. 31; 63(1):81, which is hereby incorporated herein by reference in its entirety as though fully set forth.

In various embodiments, any commercially available monoclonal or polyclonal antibody specific for 5hmC could be utilized in conjunction with the inventive methods described herein. For example the 5hmC antibody could be obtained from vendors such as Active Motif, Inc. (Carlsbad, CA), Diagenode, Inc. (Denville, NJ), GeneTex, Inc. (Irvine, CA), Sigma-Aldrich, Zymo Research, Inc. (Irvine, CA) to name a few. In some embodiments, the 5mC antibody is the antibody described in Tajbakhsh J., et al. Dynamic heterogeneity of DNA methylation and hydroxymethylation in embryonic stem cell populations captured by single-cell 3D high-content analysis. Exp Cell Res. 2015 Mar. 15; 332(2): 190, which is hereby incorporated herein by reference in its entirety as though fully set forth. Stefanovski D., et al. Prostate cancer diagnosis using epigenetic biomarkers, 3D high-content imaging and probabilistic cell-by-cell classifiers. Oncotarget 2017 Jul. 5; 8(34):57278, which is hereby incorporated by reference. In various embodiments, any commercially available monoclonal or polyclonal antibody specific for AMACR (p504s) could be utilized in conjunction with the inventive methods described herein. For example, the AMACR antibody could be obtained from vendors such as R&D Systems (Minneapolis, MN), Leica Biosystems (Nussloch, Germany), ThermoFisher Scientific, Inc. (Waltham, MA), Dako, Inc. (Agilent Technologies, Inc., Carpinteria, CA), Abcam (Cambridge, UK) to name a few. In some embodiments, the 5mC antibody is the antibody described in Witkiewicz A. K., et al. Alpha-methylacyl-CoA racemase protein expression is associated with the degree of differentiation in breast cancer using quantitative image analysis. Cancer Epidemiol Biomarkers Prev. 2005 June; 14(6):1418, which is hereby incorporated herein by reference in its entirety as though fully set forth.

Although tests described in the specific examples set forth herein involve DAPI as the primary dye for delineating gDNA, one of skill in the art would also appreciate that other dyes, which bind double-stranded DNA in a nonsequence-specific manner and can be used for gDNA quantification. These may include but are not limited to propidium iodide, the Hoechst dyes (including Hoechst 33258 and Hoechst 33342), ethidium bromide, SYBR Green, SYBR Gold, Pico Green, the SYTOX dyes (including SYTOX Green, SYTOX Blue, and SYTOX Orange), the SYTO dyes, the YOYO and TOTO families of dyes (including YOYO, TOTO, JOJO, BOBO, POPO, YO-PRO, and PO-PRO), as well as actinomycin D and 7-aminoactinomycin D (7-AAD), which could also be used for the same purposes.

In certain embodiments, the prostate tissue is obtained from a subject who has received any prostate cancer treatment including but in no way limited to radiation therapy, chemotherapy, surgery, and combinations thereof. In some embodiments, the prostate tissue is obtained from a subject who has not received one or more of the above-described cancer treatments.

In certain embodiments, the invention teaches quantifying the number of cells in the prostate tissue sample that have been identified as cancerous by implementing the foregoing testing methods, and comparing that number of cancerous cells in the prostate tissue sample to a reference number of cancerous cells in individuals who have prostate cancer and/or comparing the tested sample with a reference number of cancerous cells in individuals who do not have cancer.

Advantageously, as described in greater detail in the specific examples set forth herein, in some embodiments the inventive methods have the ability to identify tissue—that is by classic pathology (based on morphological parameters) defined as benign—as aberrant (precancerous or cancerous). This is due at least in part to the fact that the epigenetic markers, global-5mC and global-5hmC are measured. These markers can change early in cancer development. In some embodiments, the present invention teaches the detection of a field effect (also known as field defect, or field cancerization). In the course of cancer development some of the tissue areas become the obvious tumor regions and some stay as aberrant (but not tumor-specific as per current definition). These aberrant (field effect, also known as field defect) areas could be responsible for tumor recurrence (after tumor resection), and thus it is significant that they are detectable by some embodiments of the inventive methods.

In various embodiments, the invention teaches a method for treating a subject who has been diagnosed with prostate cancer according to one or more of the methods described herein. In some embodiments, the method comprises, consists of, or consists essentially of administering chemotherapy and/or radiation therapy and/or performing surgery to resect all or a portion of a tumor on the subject, or the prostate of the subject, wherein the subject was diagnosed with prostate cancer via any method described herein.

In various embodiments, the invention teaches a method that includes obtaining a sample of prostate tissue from a subject, wherein the prostate tissue includes a prostate cell; and determining if one or more cells of the prostate tissue are cancerous or benign by employing any of the methods described above.

In some embodiments, the invention teaches a non-transitory computer-readable medium that includes computer executable instructions that when executed by the processor of a computing device cause the computing device to analyze and characterize prostate cells according to any of the methods described or referenced herein. In some embodiments, the prostate cells are characterized by analyzing one or more images of prostate cells, as described herein. In some embodiments, the raw data that makes up the images is analyzed.

In various embodiments, the invention teaches a system that includes a light microscope; a computing device; and a non-transitory computer-readable medium that includes computer executable instructions that when executed by the processer of the computing device cause the computing device to analyze and characterize one or more prostate cells according to the methods described or referenced herein.

One skilled in the art will recognize many methods and materials similar or equivalent to those described herein, which could be used in the practice of the present invention. Indeed, the present invention is in no way limited to the methods and materials described.

EXAMPLES

Example 1

By way of additional background, PCa is the most common cancer among men and the second leading cause of cancer-related deaths. The incidence of PCa has tripled during the past decade, mainly because of the widespread use of serum prostate-specific antigen (PSA) testing and digital rectal examination (DRE), which has created a massive diagnostic and therapeutic burden for physicians. PSA screening detects PCa at lower stages with smaller tumor volume compared with cancer detected only by DRE. In reality, PCa is often a slowly progressive indolent tumor, predominantly in aging men, and frequently diagnosed at an early stage with localized tumors that are unlikely to cause morbidity or death. However, a low percentage of PCa cases are more aggressive leading to accelerated tumor growth and metastasis.

Problem with Current PCa Testing

PCa, PSA testing may lead to over-diagnosis and possibly over-treatment of indolent tumors. Hence PSA test results need to be carefully interpreted along with other pathological parameters, and implementation of PSA screening is no longer recommended. Understandingly, there is an urgent unmet need for biomarkers to complement PSA for screening and better patient stratification. This would primarily include differentiation of aggressive disease that needs to be treated immediately versus indolent cancers that can be primarily managed by active surveillance. Thus, ideally the biomarker(s) should have a prognostic value for clinical utility. The standard diagnostic technique for screening of PCa is histopathological review of prostate tissue collected through needle biopsy. 12-core or 14-core transrectal ultrasound-guided prostate needle biopsy (TRUS) is the most prevalent method for initial biopsy from patients with an elevated serum PSA level.

Currently, although PSA levels and PSA kinetics are gathered, they are not used to define cancer progression on active surveillance. Biopsy classification using a revised version of the original Gleason grading system has emerged as a more meaningful endpoint for monitored men. PCa must meet three criteria to be deemed insignificant: the biopsy must receive only Gleason score (GS) 6 (3+3) histology, constitute an organ confined primary tumor as diagnosed by magnetic resonance imaging (MRI) of the prostate, and have a core volume (positive for tumor) of 50% or less (determined by histology). Higher-grade tumors (GS7 and higher) imply a significantly elevated likelihood of clinical progression. Currently, prostate biopsy remains the only method to ascertain prostate cancer grade.

Nevertheless, when low-grade PCa is diagnosed on needle biopsy, there is a risk of undergrading because of a sampling error, which occurs when a higher-grade component in the prostate gland is being missed during the biopsy process. In about 20-30 percent of the time, when a patient has a GS6, there may be higher-grade tissue present in the rest of the prostate. This relatively high frequency of occult tissue has been shown in a meta-analysis of 23 studies (with 100 cases or more) in which ~35% of all cases were found to have a higher grade at paired radical prostatectomy.

Concerns about false-negative results in conjunction with persistent risk factors, such as increased PSA, often leads to repeated biopsies. The negative impact of the limited precision of histopathology may subject cancer-free men to additional invasive biopsy procedures with associated negative effects, including anxiety and the risk of urosepsis. This re-emphasizes the necessity of an additional diagnostic/prognostic indicator of prostate malignancy in biopsy tissue that could also avoid unnecessary rebiopsy.

Correlation of Epigenetic Aberrations (e.g. DNA Methylation) with Cancer Types

There is a body of evidence, which shows that epigenetic aberrations such as altered DNA methylation and related changes in histone-tail modification patterns amongst other features correlate with several cancer types, including PCa. Epigenetic changes are by now known to occur early in cellular transformation and cancer development. Cancer cells usually display hypermethylation of a relatively small number of single gene promoters, mostly in gene-rich genomic regions termed CpG islands, leading to silencing of certain tumor suppressors involved in cell-cycle regulation, DNA mismatch repair, cellular differentiation, and apoptosis. Hypermethylation of the glutathione S-transferase pi (GSTP1) gene promoter has been observed in nearly 90% of all prostatic carcinomas but not in benign hyperplastic tissue. Other well-characterized hypermethylated genes in PCa include RASSF 1A, CDH1 and CDKN2A. Promoter hypermethylation is often coexistent with hypomethylation at the global DNA (gDNA) level. A malignant cell can contain 20-60% less genomic 5-methylcytosine (5mC) than its normal counterpart. The loss of methyl groups is achieved mainly by hypomethylation of repetitive DNA sequences, which count for more than 90% of the human genome, including transposable elements (-48% of genome) such as short and long interspersed nuclear elements (SINES and LINES, respectively), largely acquired as retroviruses throughout evolution. Global demethylation is also clinically relevant, as demonstrated by associations between clinical outcome and global methylation levels in a number of cancer types. Global hypomethylation seems to be related to cancer progression, since loss of global methylation tends to become more pronounced as precancerous lesions progress. As for PCa, global hypomethylation correlates with both tumor development and progression. Global hypomethylation is often accompanied with the under-presentation of repressive heterochromatin-associated histone marks, predominantly histone-3 lysine-methylation such as H3K27me3 (facultative heterochromatin) and H3K9me3 (constitutive heterochromatin). Compared to promoter CpGs global hypomethylation has been less investigated as a biomarker, despite the fact that it is ubiquitous and much more pronounced in cancers than is gene-promoter hypermethylation.

Methods for Quantification of DNA Methylation and Histone Modification Patterns

The global changes in DNA methylation and histone modification patterns can be visualized and quantified by high-resolution light microscopy in conjunction with computer-assisted image analysis. Besides DNA methylation also genome-wide changes in cellular DNA hydroxymethylation are associated with various cancers.

Recently, we had only briefly disclosed the capability of newly developed 3D high-content analysis to perform DNA methylation phenotyping of cells towards characterization of human prostate tissue heterogeneity. However, biological differences across epigenetic and non-epigenetic biomarkers support the use of several markers in a cancer detection assay. Described in greater detail herein below is are parallel cell-by-cell analytical techniques—using3D high-content imaging, chromatin-associated epigenetic in combination with validated PCa-relevant markers, and mathematical-statistical principles for analysis of large amounts of imaging data—to generate novel detailed maps of biomarker heterogeneity in patient tissues and assess their potential in PCa diagnosis and prognosis.

Example 1 Methods: Evaluation of Biomarkers I and II

Described herein below is the evaluation of two sets of biomarkers that are novel in their combination. The first set of PCa-related markers (Biomarkers I) comprised DAPI representing gDNA, the two cytosine variants 5mC and 5hmC, and AMACR). The second panel (Biomarkers II included DAPI, SAFB, H3K9me3, H3K27me3, and the fraction of AR that was present in the cell nucleus as nuclear AR (nAR). DAPI was used in both sets also for technical reasons, i.e. to delineate the nuclear region of interest; a standard procedure to enable the segmentation of cell nuclei and the creation of an image mask in order to also retrieve nuclear signals of the other biomarkers in the other channels, as can be inferred from the methods section. The strategy for this study was three-fold. First, exploring the degree of changes (variance and covariance) of the two sets of biomarkers in correlation with tissue cancer pathology (degree of malignancy) was of interest. Based on that it was also an aim to determine which compartment would exhibit an overall comparatively higher differentiality regarding the applied markers. Second, it was important to evaluate the potential of included nuclear biomarkers representing epigenetic features in combination with established markers of prostate tissue pathology, to discriminate between benign (normal, non-cancerous) and aberrant (malign, cancerous) cells of prostatic origin using high-resolution high-content imaging. Utilizing gleaned knowledge on the performance of the two marker panels, the third objective was to characterize prostatic tissue based on its composition of benign and aberrant cells, using both biomarker panels. This characterization entails the classification of prostatic tissue and the prediction of tissue/cancer development, i.e. cancer indolence versus more aggressive progression, at first diagnosis (needle biopsy 1).

Towards these goals archived tissues from 9 subjects were used, as well as two well-characterized human cell cultures of prostatic origin: human prostate epithelial cells (HPrEpiC) as normal primary cells, and LNCaP, an androgen-sensitive prostate cancer cell line. The selection of cultured cell models was also driven by the fact that the two types of cells were previously extensively studied in terms of proliferation and in situ global DNA methylation patterns. In this sense both cell types had shown characteristic properties of their respective categories as normal and cancer cells. Furthermore, HPrEpiC, which undergo proliferative senescence in culture, were the only reliable source of epithelial cells of prostatic origin in the presently reported study that had been proven to exhibit a normal phenotype, considering that morphologically benign-appearing biopsied tissue—that is generally obtained from patients with signs of PCa—may already carry epigenetic abnormalities. The longitudinal analysis with most of the archived patient specimens comprised tissue samples that were collected at different diagnostic time points, including diagnosis—initial trans-rectal needle biopsy (biopsy 1) and if available a follow-up biopsy (biopsy 2)—and prostatectomy, as shown in Table 1.

TABLE 1

Patient specimens used in the study.

| Name | Biopsy 1 | Biopsy 2 | Prostatectomy |
|---|---|---|---|
| Development Specimens | | | |
| Patient 1 | Atypical glands + small focus of cancer, GS6 (3 + 3) | AC, GS6 (3 + 3) | Stage III (pT3a), GS7 (3 + 4) |
| Patient 2 | Lots of AC, GS7 (4 + 3) | | Stage II (pT2c), GS7 (3 + 4) |
| Patient 3 | Benign | AC, GS7 (4 + 3) | Stage III (pT3a), GS7 (3 + 4) |
| Patient 4 | Lots of AC, GS6 (3 + 3) | | Stage II (pT2c), GS7 (3 + 4) |
| Patient 5 | Lots of AC, GS6 (3 + 3) | | Stage III (pT3b), GS6 (3 + 3) |
| Validation Specimens | | | |
| Patient 5 | | | Benign tissue distal from tumor region |
| Patient 6 | Lots of AC, GS6 (3 + 3) | | Stage II (pT2c), GS6 (3 + 3) |
| Patient 7 | Lots of AC, GS6 (3 + 3) | | Stage II (pT2c), GS6 (3 + 3) |
| Patient 8 | Lots of AC, GS7 (3 + 4) | | Stage II (pt2c), GS7 (3 + 4) |
| Patient Z | | | Benign tissue distal from tumor region |
| HPrEpiC | Isolated from normal human prostate tissue, cytokeratin 18 and 19 positive | | |
| LNCaP | Isolated from human needle biopsy, androgen-sensitive prostate adenocarcinoma cells | | |

Differential Imaging and Analysis of Tissues

The high-content assay and analysis was performed on a three-dimensional quantitative DNA methylation imaging (3D-qDMI) platform that was previously introduced (See Gertych A, Wawrowsky K A, Lindsley E, Vishnevsky E, Farkas D L, Tajbakhsh J.

Automated quantification of DNA demethylation effects in cells via 3D mapping of nuclear signatures and population homogeneity assessment. Cytometry A 2009; 75: 569-83; Oh J H, Gertych A, Tajbakhsh J, the content of which is incorporated herein by reference in its entirety. Nuclear DNA methylation and chromatin condensation phenotypes are distinct between normally proliferating/aging, rapidly growing/immortal, and senescent cells. Oncotarget. 2013; 4: 474-93; and Zha S, Ferdinandusse S, Denis S, Wanders R J, Ewing C M, Luo J, De Marzo A M, Isaacs W B, the content of which is incorporated herein by reference in its entirety. Alpha-methylacyl-CoA racemase as an androgen-independent growth modifier in prostate cancer. Cancer Res. 2003; 63: 7365-76.), the content of which is incorporated herein by reference in its entirety.

Figure 1:
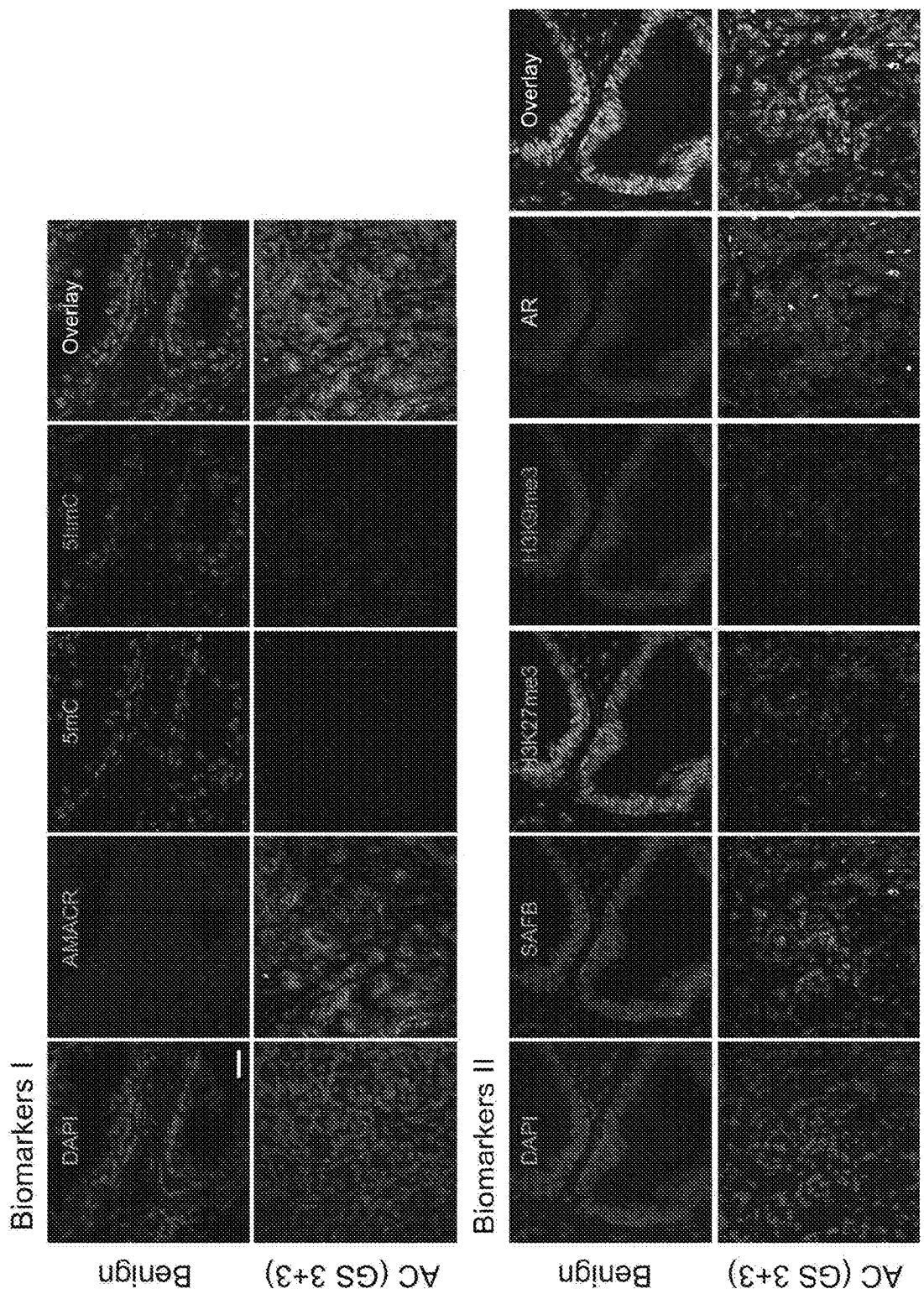
FIG. 1 depicts, in accordance with various embodiments of the invention, differential levels and cellular heterogeneity of the two biomarker panels Biomarkers I and II between biopsied benign and cancerous prostatic tissues (represented by adenocarcinoma (AC) with Gleason score 6 (GS6), as visualized by confocal scanning microscopy. Each marker (false-colored) was recorded in a separate channel. For each tissue sample all channels—including the multi-color overlay image—are presented as maximum intensity projections. Biomarkers I: significant increase in alpha-methylacyl-CoA racemase (AMACR) levels and simultaneous loss of the two epigenetic DNA modifications 5-hydroxymethylcytosine (5mC) and 5-hydroxymethylcytosine (5hmC) in both basal and luminal epithelial cells in AC versus benign tissue; luminal cells seemingly exhibit a stronger loss of 5hmC compared to basal cells. Biomarkers II: The loss of the two suppressive chromatin-state markers tri-methylated lysine 9 on histone 3 (H3K9me3) and tri-methylated lysine 27 on histone 3 (H3K27me3) appears stronger than for chromatin-associated scaffold attachment factor B (SAFB), which exhibits a more heterogeneous decrease among cells. As expected androgen receptor (AR) levels are highly elevated in AC versus benign tissue. Scale bar is 10 µm.

The technology constitutes a multiplexed image-cytometric approach, by which fluorescence signals of simultaneously visualized nuclear targets, generated through established immunocytochemistry and light microscopy, are extracted from 3D images to visualize and measure changes in global epigenetic markers such as DNA methylation/hydroxymethylation and other molecular targets in thousands of cells in parallel. This capability to analyze cell populations on a per-cell basis is a powerful means in addressing cell population heterogeneity in tissues. Within this context, the application of high-resolution confocal microscopy in the range of 0.1 µm-1 µm allowed for separately acquire images from the two major tissue compartments, i.e. the epithelium and the stroma, as well as mixed areas that also entailed border regions between the two compartments. Hence for each subject each tissue sample was divided into four categories based on the represented tissue compartments: epithelium only (E), major epithelium with minor stroma (E+s), equal portions of epithelium and stroma (ES), and stroma only (S), as shown in FIG. 1.

Figure 2:
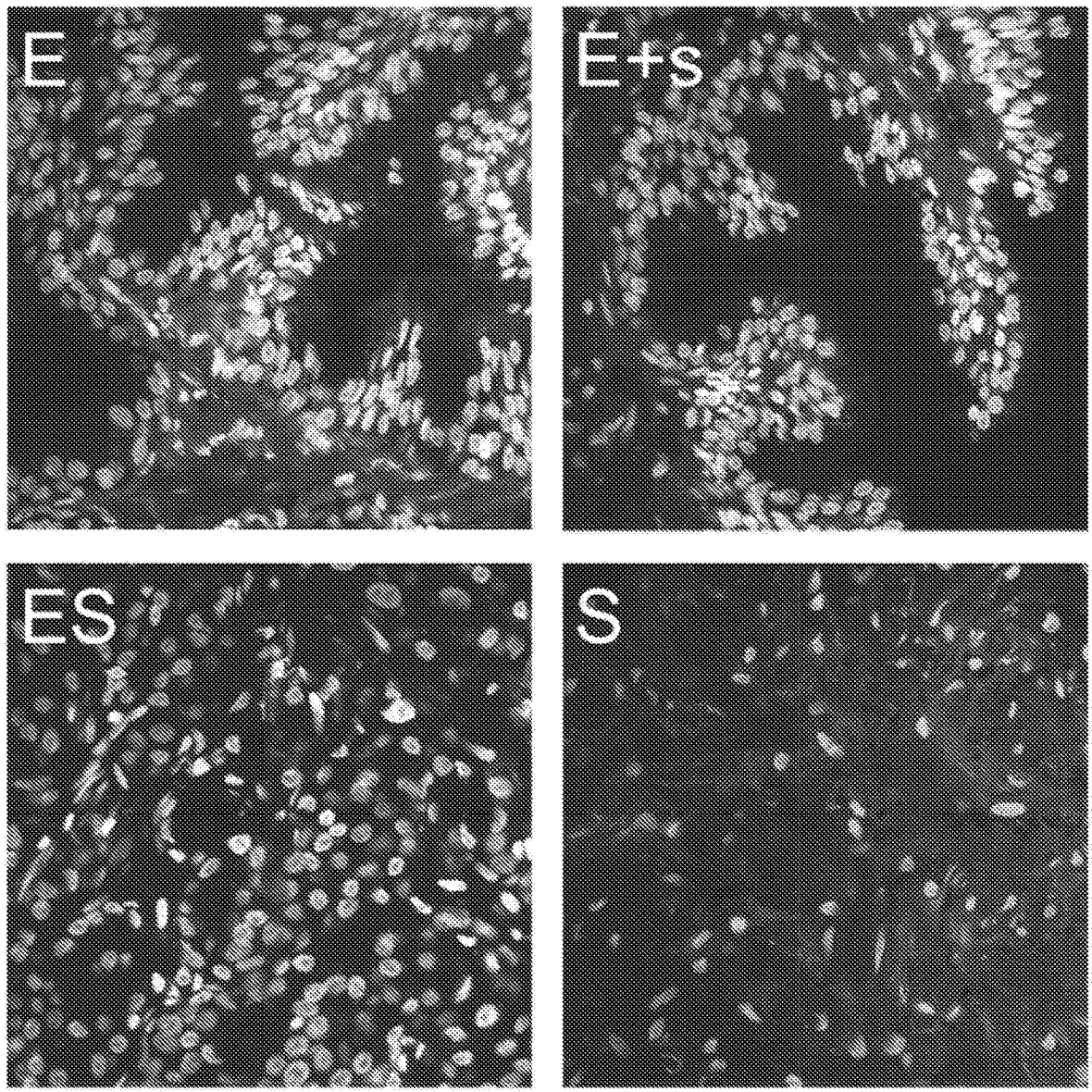
FIG. 2 depicts, in accordance with various embodiments of the invention, prostate tissue imaging showing optical mid-sections in the 4,6-diamidino-2-phenylindole, dihydrochloride (DAPI) channel. Imaging was performed to acquire four categories of tissue frames corresponding to a sampling spectrum of epithelial and stromal compartments: epithelia only (E), epithelia with minor bordering stroma (E+s), mixed epithelia and stroma at various ratios (ES), and stroma only (S).

Hematoxylin & eosin (H&E) stainings from the matching middle sections of the tissues have been used to identify tissue regions for confocal imaging (FIGS. 8A-8D). Overall, an increase in DAPI (gDNA), AMACR, and nAR (nuclear portion of AR), and reciprocally a decrease in 5mC, 5hmC, H3K9me3, and H3K27me3 were explored. In the case of SAFB, general trends were not observed across imaged cells of adenocarcinoma (AC) tissue. Subsets of cells appeared to show more or less SAFB than the average abundance (intensity) of this protein in the epithelial cells of histopathologically (structurally) benign prostate tissues. However, tumor areas displayed a higher heterogeneity of SAFB than the morphologically intact (benign) epithelium. Therefore, the imaging results were in agreement with previous findings that had reported similar trends of the individual markers in association with the degree of tissue malignancy. FIG. 2 provides the visual impressions regarding the intensities of the four markers in pathologically different tissues.

Phenotypic Biomarker Heterogeneity in Tissues

In addition to observations at the microscopic level and the report on average changes of biomarker intensities, utilizing the asset of single-cell data (gathered in this study) to conduct a systematic quantitative analysis of marker heterogeneity in the different pathological tissues was of interest. Because the data were derived from tissues that had been excised at different time-points it was not possible to conduct a continuous assessment of marker-covariance over time. Previous studies to characterize cell phenotypes in complex cell populations such as differentiating embryonic stem cells (ESC) using big imaging data, indicated that principle component analysis is a valuable statistical approach to determine marker variance in multi-parametric assays. Principle component analysis enables the reduction of observed variables, while preserving a large portion of the variance in the data. Using principle component analysis, the newly produced variables were derived in decreasing order of importance pertaining to the amount of variation they explain of the original variables. For example, principle component 1 explains for as much of the variability of the original data as possible. The second principle component explains as much of the remaining variance as possible under assertion that it is not correlated to principle component 1, etc. This reduction is useful as the data could be graphically summarized, instead of exploring the covariance/correlation of the pairwise relationship between the markers within each of the two marker sets in this study.

Figure 3A:
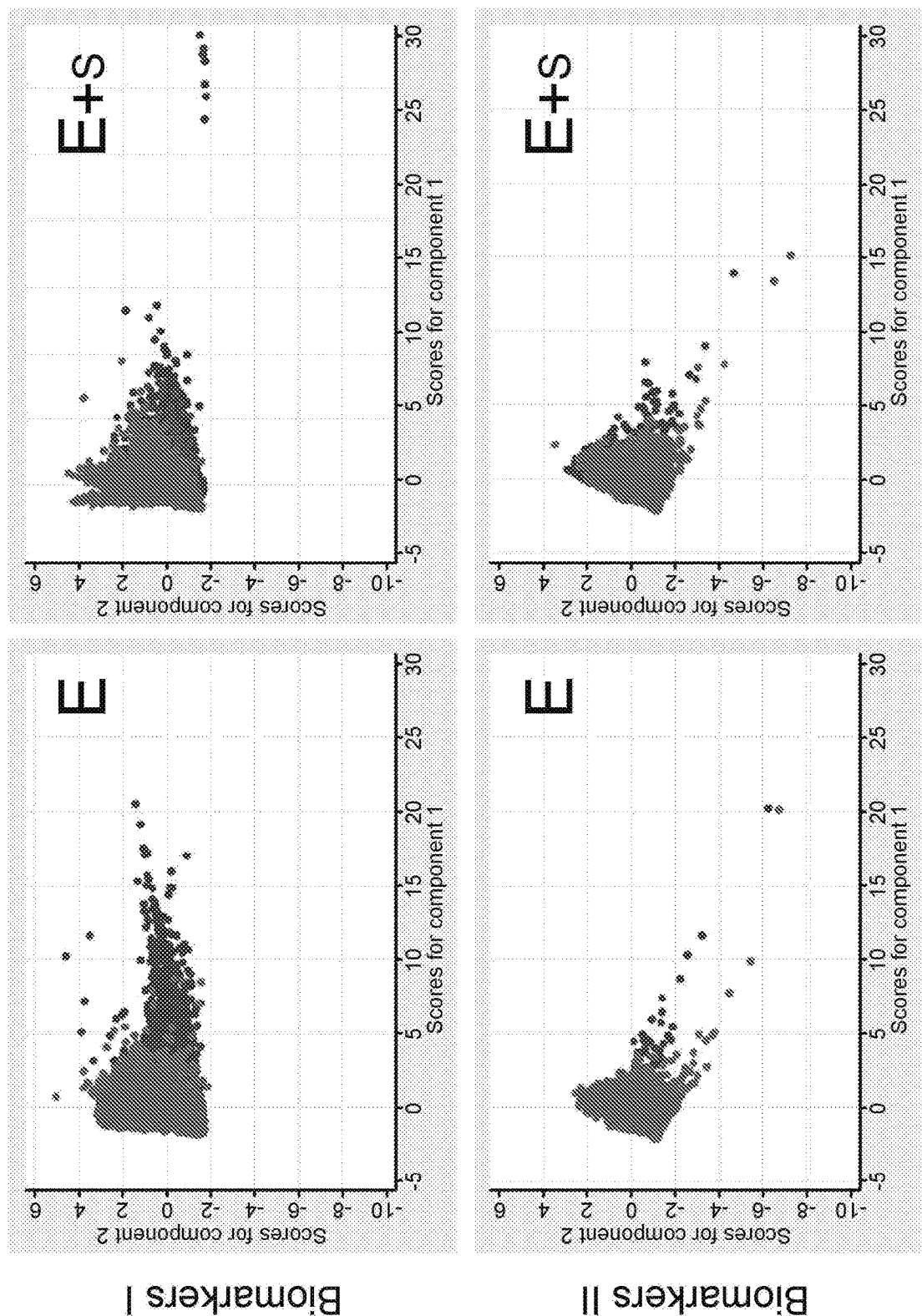
FIGS. 3A-3B depict, in accordance with various embodiments of the invention, comparative tissue compartment-specific results of principle component analysis (with two components) for Biomarkers I and II. The data was separated into subsets representing the first biopsy (blue), the second biopsy (red), and finally prostatectomy (green). Each dot represents one cell. The results show a high overlap when epithelial and stromal compartments are analyzed together (ES). The overlap is reduced in the case of only a minor involvement of stroma (E+s). The best segregation is seen when the epithelial compartment is analyzed by itself, indicating the highest change (variance) for the analyzed markers. The latter subdata is missing from two biopsies, as most patients for which epithelial (E) compartments could be analyzed were initially diagnosed with lots of AC and thus only underwent one biopsy prior to prostatectomy.
Figure 3B:
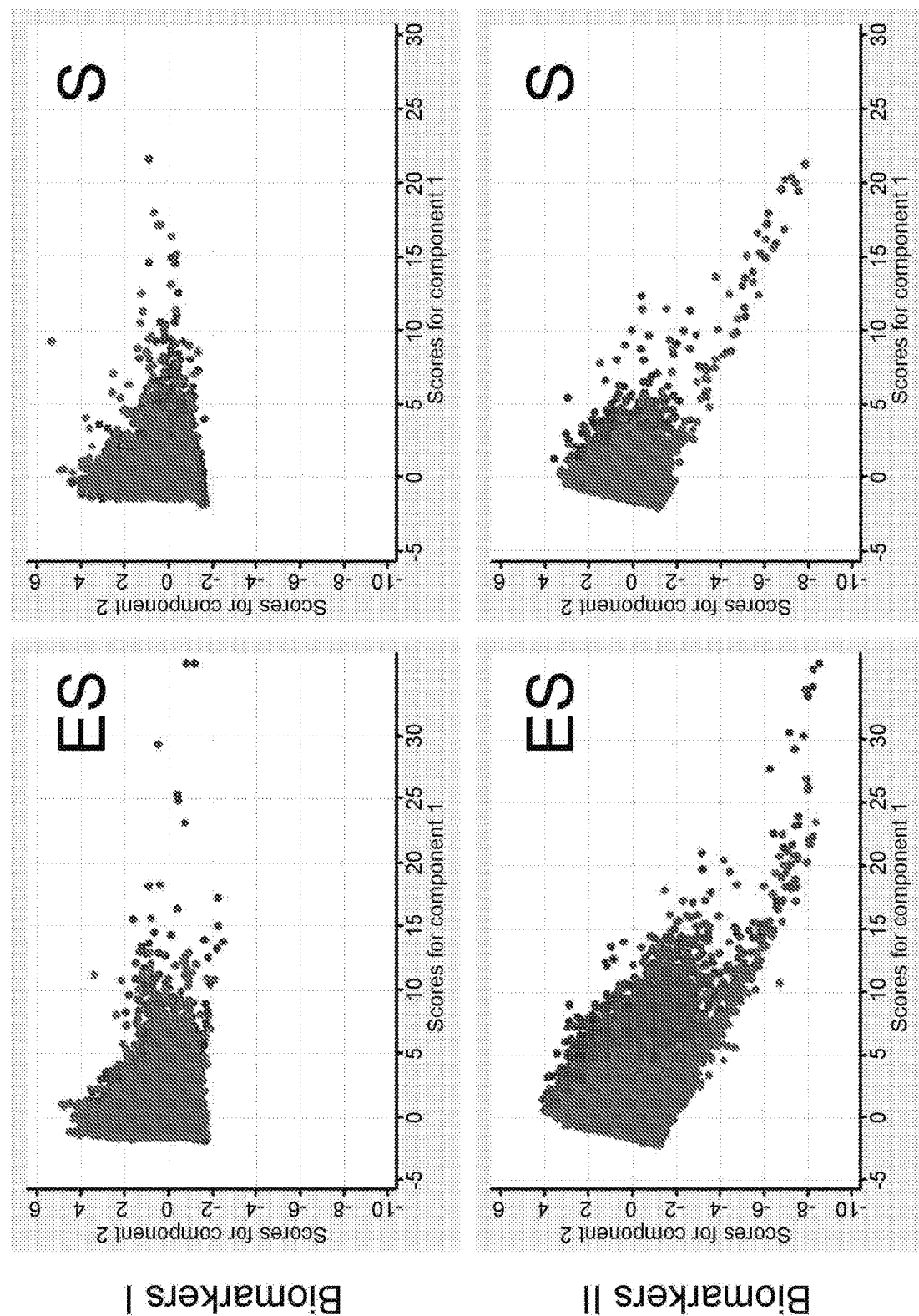

FIGS. 3A-3B illustrates the degree of compartment-specific data segregation for Biomarkers I (DAPI, AMACR, 5mC, and 5hmC) and Biomarkers II (DAPI, nAR, SAFB, H3K9me3, and H3K27me3) across all exploratory tissue samples from Patients 1 to 5. For Biomarkers I, the highest covariation was found in the epithelial compartment. This variation correlatively diminishes with increasing proportions of stromal regions. As for the abovementioned biomarkers the stromal compartment by itself did not show any significant covariation. The loading matrix (Table 10) indicates that the major drivers of principle component 1 (highest variable markers) are 5hmC and AMACR at about equal weight, followed by 5mC, while principle component 2 is dominated by DAPI variables. In comparison, Biomarkers II did not segregate well (FIGS. 3A-3B). In this case principle component 1 was majorly influenced by H3K27me3 and nAR at about equivalent power, followed by SAFB. Principle component 2 was driven by DAPI, as shown in Table 11.

Figure 4:
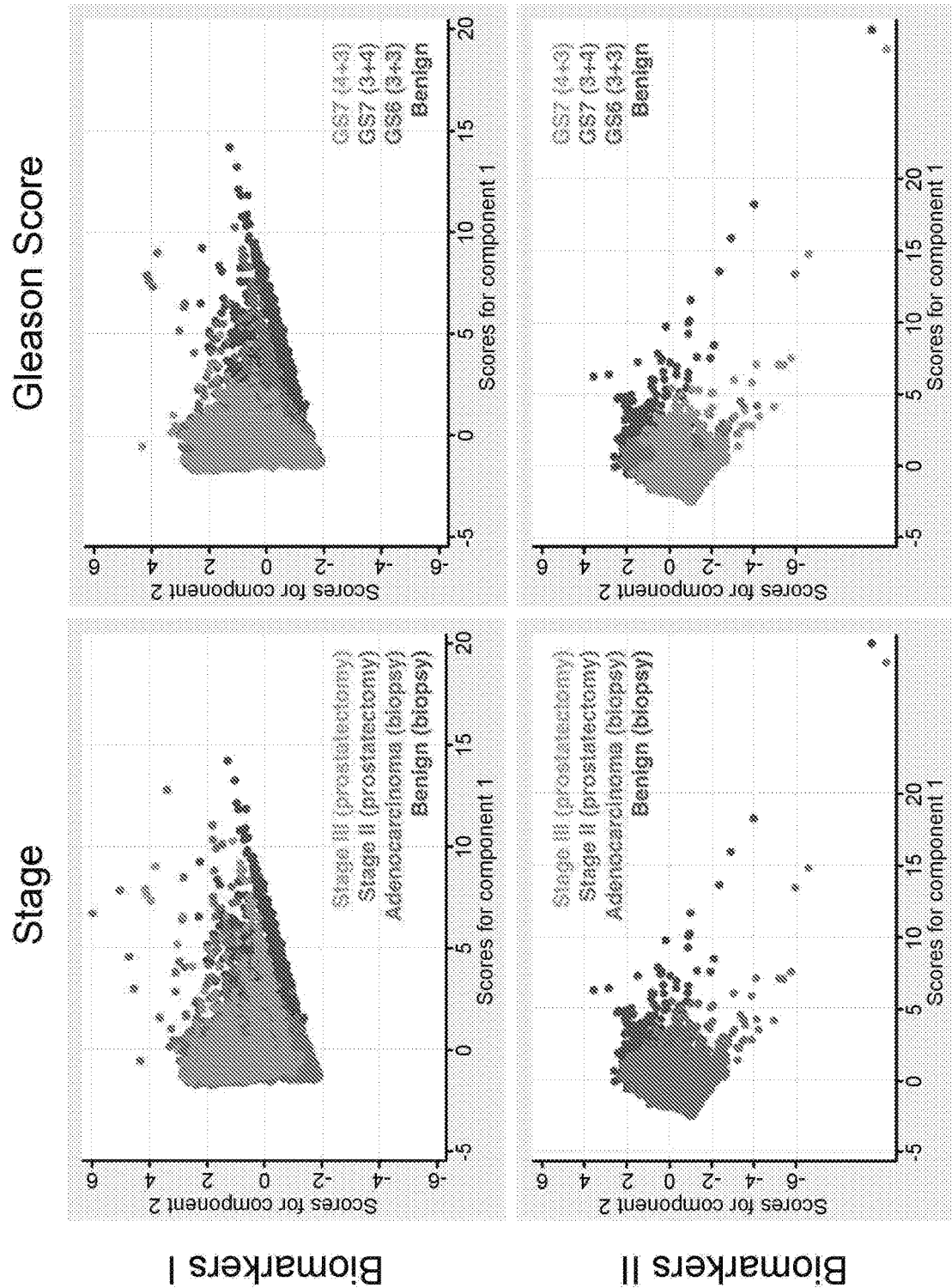
FIG. 4 depicts, in accordance with various embodiments of the invention, comparative results of principle component analysis (with two components) for Biomarkers I and II according to pathological categories or GS. The analysis was performed with cells located only in the epithelial compartment, which showed highest differential results in the first analysis (FIGS. 3A-3B).

Next, principle component analysis was performed using only data derived from the epithelial compartment to explore any covariation of the abovementioned markers in association with tissue malignancy. Tissue malignancy was distinguished either by PCa pathological categories (benign, AC at biopsy, and stage II and stage III cancer at prostatectomy) or by Gleason scores (GS) including GS6 (3+3), GS7 (3+4), and GS7 (4+3). In the relevant FIG. 4, the composite plots illustrate that for both biomarker sets there seems to be no significant difference in data segregation between the two tissue classifications. However, there is a strikingly better segregation of the data for Biomarkers I compared with Biomarkers II.

Figure 5A:
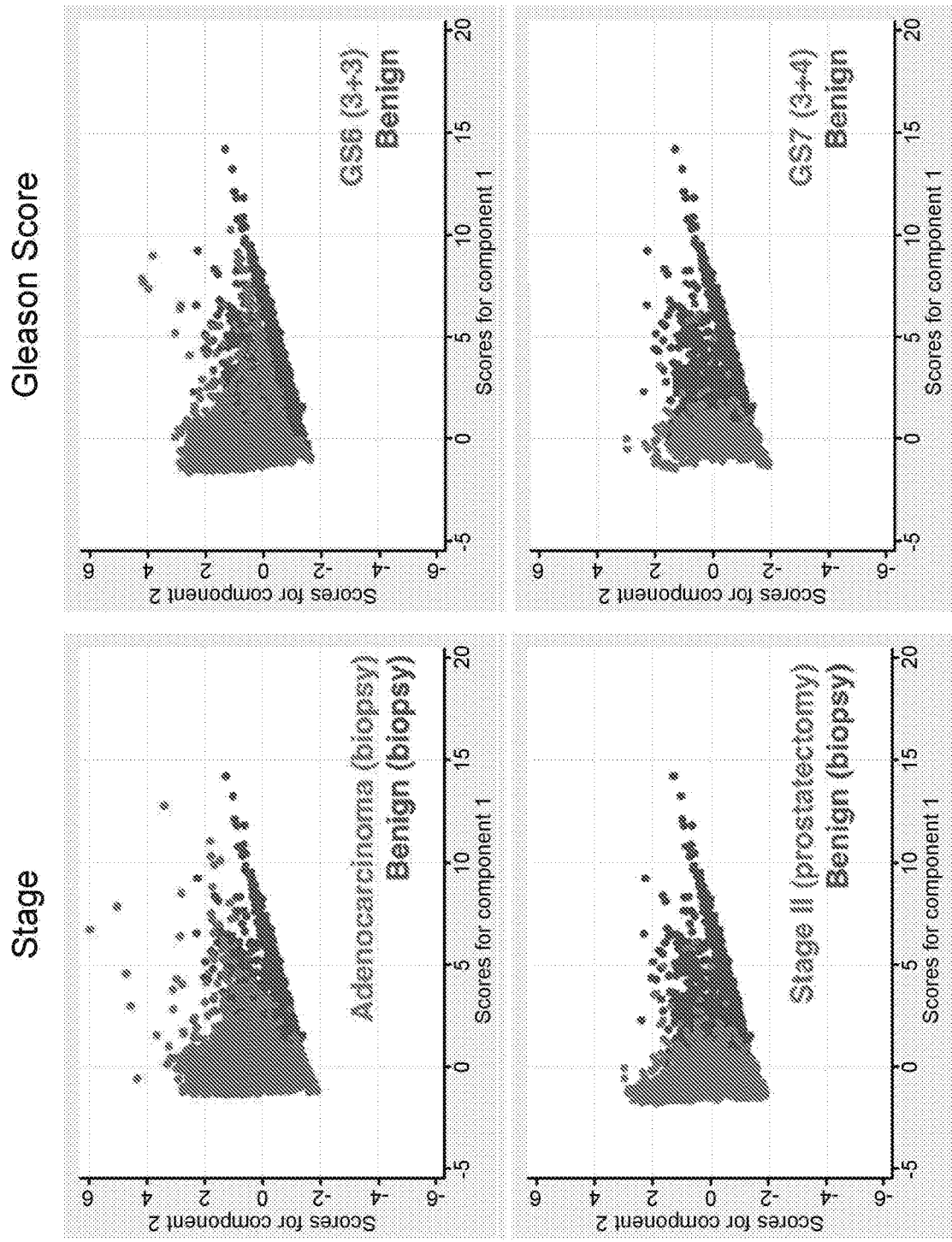
FIGS. 5A-5C depict, in accordance with various embodiments of the invention, pairwise comparative results of principle component analysis for Biomarkers I between the two types of tissue characteristics (used in pathological diagnosis); i.e. pathological categories versus GS.
Figure 5B:
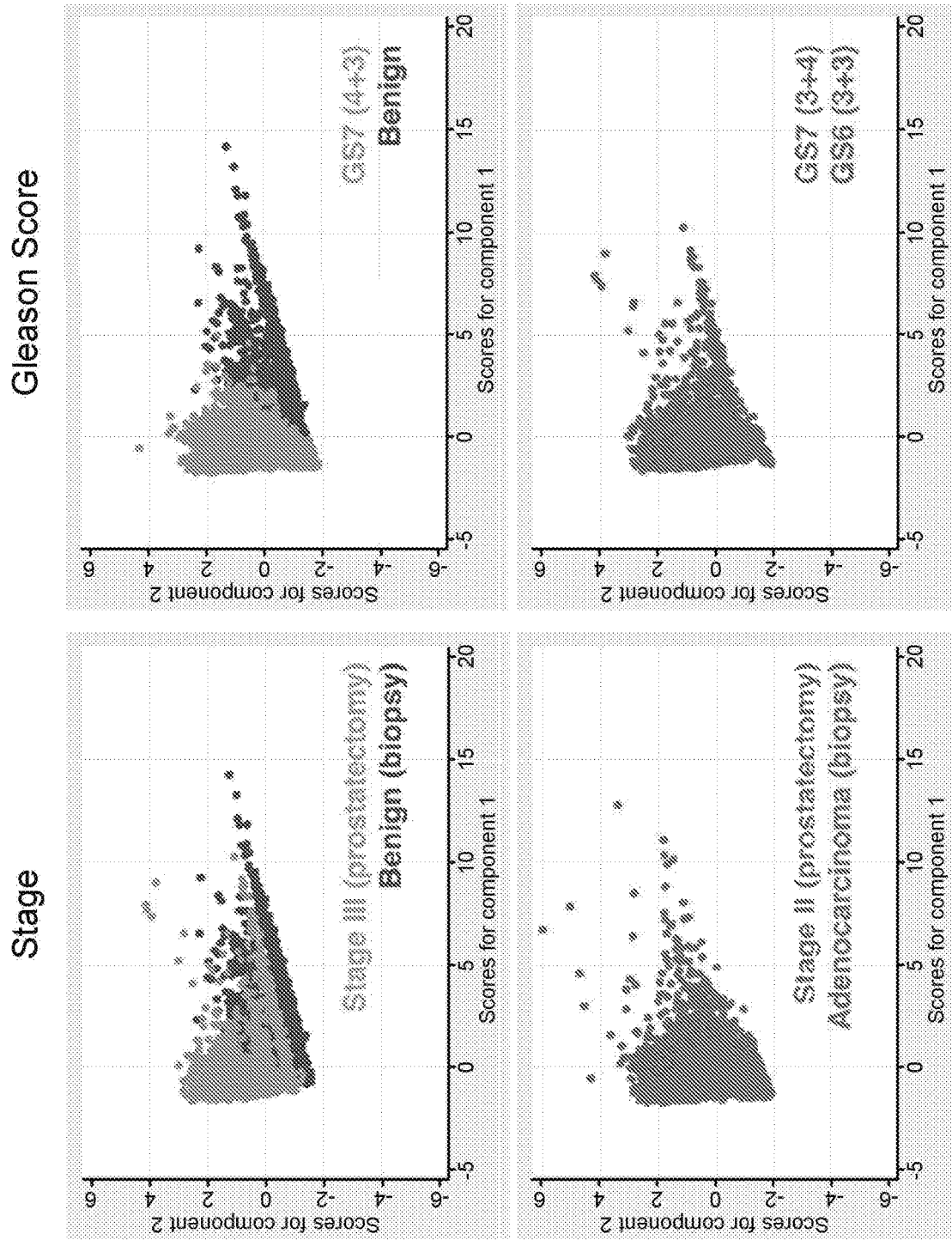
Figure 5C:
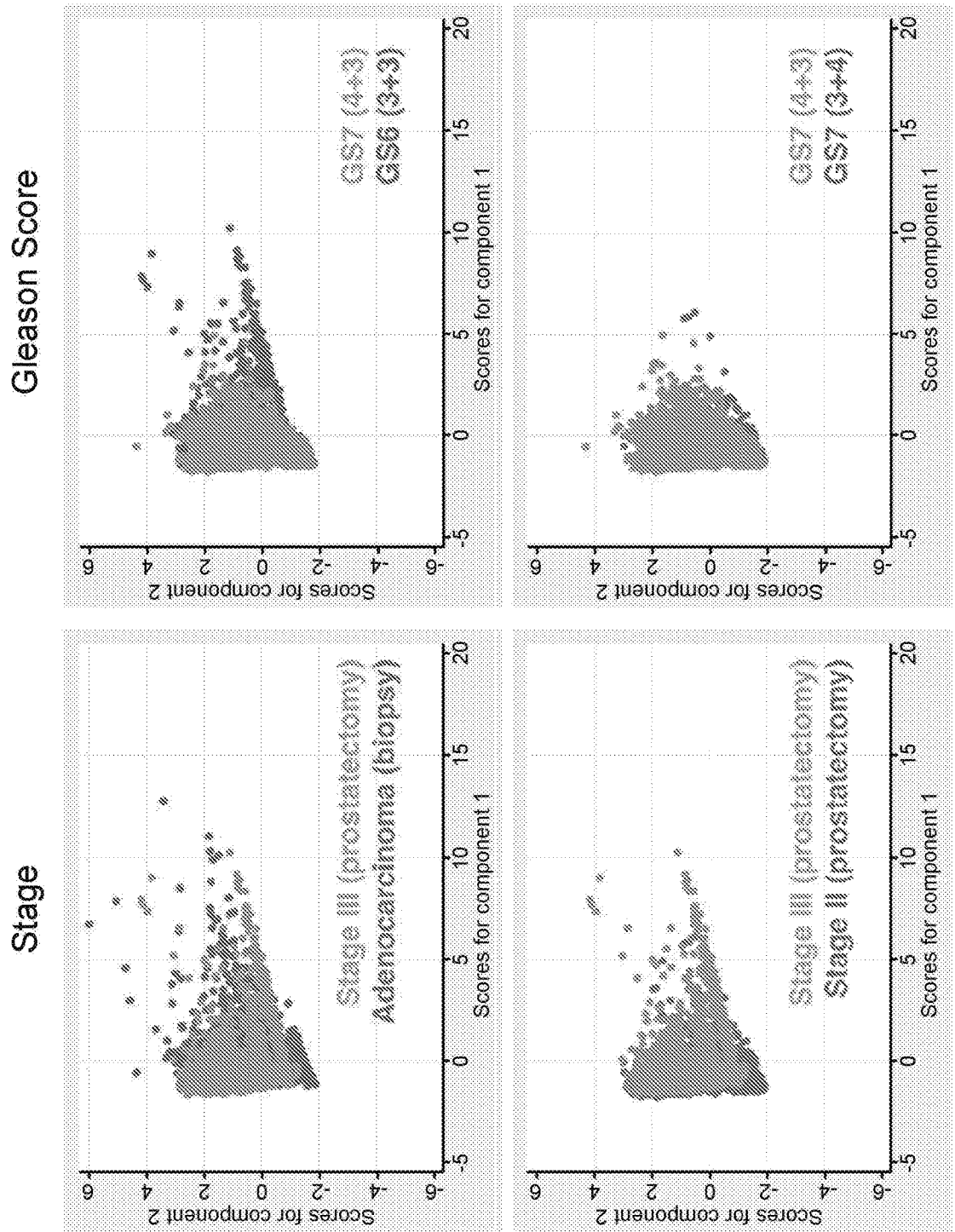

The pairwise display of the abovementioned results for Biomarkers I revealed more detailed information on the two comparative tissue classifications (FIGS. 5A-5C). The results show significant changes of the markers between the morphologically benign tissue and AC, diagnosed through needle biopsy as well as benign versus stage II and stage III cancer, the latter two conditions diagnosed after prostatectomy. The data for AC is slightly more overlapping with stage II and even more so with stage III, indicating that biopsied AC tissue used in this study must have had very similar values for Biomarkers I compared with prostatectomy samples of patients diagnosed with stage II and even more so with stage III cancer. This is conceivable as stage II plotted against stage III exhibited also a significant overlap. When GS was utilized for tissue characterization, an overall better performance (segregation) of Biomarkers I was observed. Similarly to when cancer staging and/or pathological categories were used as the diagnostic index, benign tissue clearly distinguished itself from cancerous prostate tissues, i.e. GS6 and GS7. A significant segregation was also found between GS6 and two GS7 tissue types. However, a notable overlap could be observed between GS (3+4) and the supposedly more aggressive GS (4+3), indicating that only minor differences in Biomarkers I seem to exist between the two cancer types with a minor or major component 4.

Distinction between Cancer and Non-Cancer Cells

Figure 6:
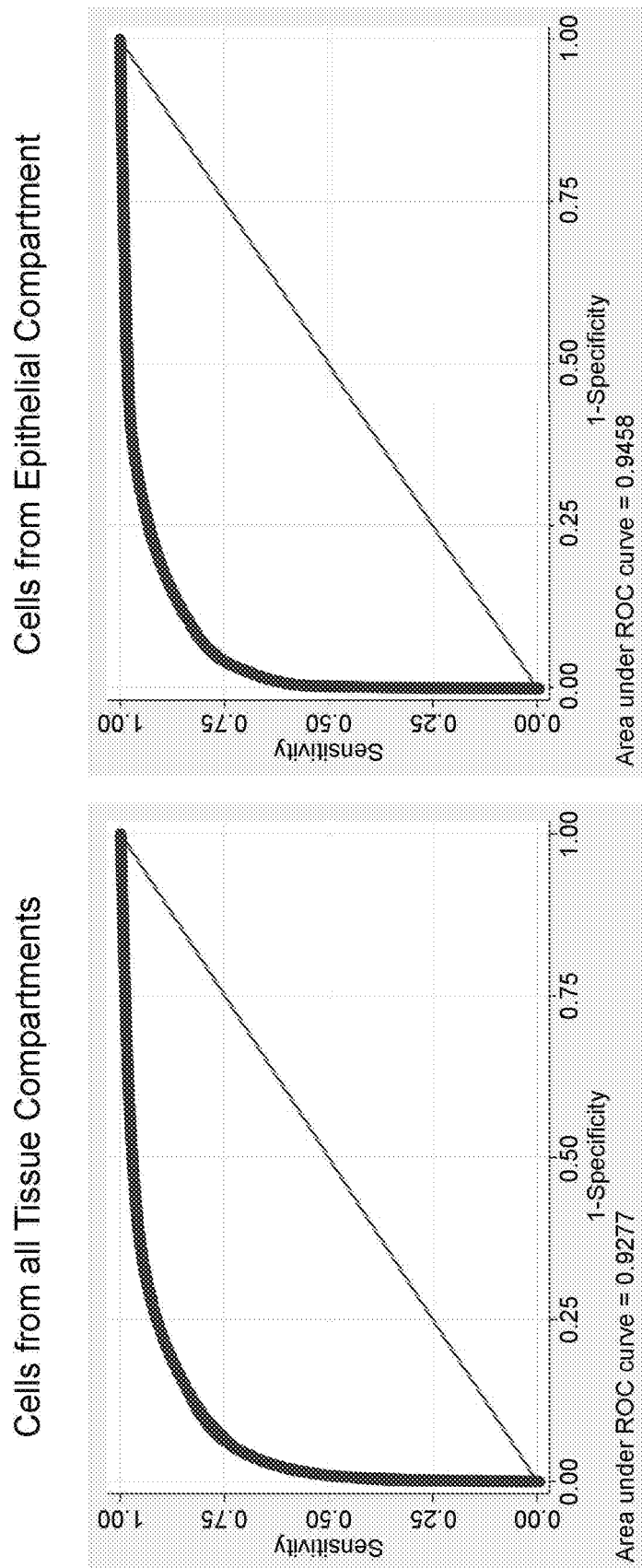
FIG. 6 depicts, in accordance with various embodiments of the invention, performance of logistic regression model with the development data set and Biomarkers I, utilizing epithelial cells only (A) and all subsets of all imaged cells (B).

Towards the second objective, two logistic regression models were explored. For both models the data was divided into a developmental subset using tissue data of Patients 1 to 5, and a validation test set that comprised data from: a) the two cultured cells, and Patients 6, 7 and 8, as well as two prostatectomy tissue samples isolated from areas distant from the tumor that had normal appearance based on H&E staining (per expert pathological diagnosis). The latter specimens were from Patient 5 and separately from another patient (Patient Z). For the developmental set, tissue from Patient 3 biopsy 1—pathologically classified as benign—was used as healthy control. The first logistic regression model was based only on cells that were found within the epithelial tissue compartments. Most of the channel intensities showed to have a significantly skewed distribution. All channel intensities were log-transformed prior to application in the logistic regression model. In total, a set of 17,881 cells were employed of which 3,829 were rated as normal and 14,052 as aberrant (cancerous) cells. All of the four Biomarkers I showed significant impact on the overall probability for cancer given their individual probability (Table 2). Log-transformed unit changes in marker intensities resulted in enormous alterations in the odds ratio (OR) for cancer: for DAPI a 7-fold increase (95% Cred. Int.: 6.7-7.8 OR), for AMACR an 80% decrease (95% Cred. Int: 82%-77%), for 5mC a 98% decrease (95% Cred. Int: 97.5%-99.2%), and for 5hmC a 3-fold increase (95% Cred. Int: 2.5-3.4 OR). Based on the probability of cancer using a cutoff point of 0.75, this model resulted in 88% sensitivity and 84% specificity, whereby 87% of the cells were accurately classified (FIG. 6).

The validation subset of data showed that the logistic model classified 81% of the HPrEpiC as non-cancerous (normal). Analogously, 99% of the LNCaP cells were classified as cancerous (Table 3A). Interestingly, the supposedly "normal/benign" tissues that were isolated distally from the tumor region in Patients 5 and Z during prostatectomy, were classified as containing an overwhelming portion of cells that exhibited an aberrant (cancer-type) Biomarker I profile: 99.9% in Patient 5 and 77% in Patient Z (Table 3B). In data of Patient 6, which was not part of the development model, 92% of cells in the first biopsy sample and 95% of the cells in the prostatectomy sample were identified as being transformed (cancerous, Table 3C). Finally, for Patient 7 the logistic model estimated that 99% of cells isolated during the first biopsy were cancer-like. The model based on cells from the epithelial compartment only, estimated that 94% of the cells from Patient 8 were abnormal (Table 3D).

TABLE 2

Logistic regression model coefficients for epithelial cells only.

| Marker | Odds Ratio | Std. Err. | z | P > z | Conf. | [95% Interval] |
|---|---|---|---|---|---|---|
| lnDAPI | 7.224606 | 0.2921743 | 48.9 | <0.0001 | 6.674063 | 7.820565 |
| lnAMACR | 0.199478 | 0.0132372 | −24.29 | <0.0001 | 0.1751499 | 0.2271852 |
| ln5mC | 0.0199724 | 0.0017131 | −45.63 | <0.0001 | 0.0168818 | 0.0236286 |
| ln5hmC | 2.95159 | 0.2216339 | 14.41 | <0.0001 | 2.547649 | 3.419578 |
| _cons | 490131.5 | 201505.3 | 31.87 | <0.0001 | 218958.8 | 1097142 |

TABLE 3

Predictions of Logistic model based on epithelial cells only. (A) cancer and benign cell types; (B) pathologically defined benign tissue isolated during prostatectomy of Patients 5 and Z; (C) Patient 6: prediction of cancer at phase of tissue isolation. (D) tissue isolated during initial biopsy from Patients 8 and 9.

| | Presence of cancer cell | | |
|---|---|---|---|
| ID | No | Yes | Total |
| A | | | |
| HPrEpiC | 1,800 | 266 | 2,066 |
| % | 87.12 | 12.88 | 100.00 |
| LNCaP | 148 | 17,289 | 17,437 |
| % | 0.85 | 99.15 | 100.00 |
| B | | | |
| Patient 5 | 3 | 11,582 | 11,585 |
| % | 0.03 | 99.97 | 100 |
| Patient Z | 2,168 | 7,206 | 9,374 |
| % | 23.13 | 76.87 | 100 |

| | Presence of cancer cell | | |
|---|---|---|---|
| Phase | No | Yes | Total |
| C | | | |
| B1 | 359 | 2,360 | 2,719 |
| % | 13.2 | 86.8 | 100 |
| P | 1,488 | 18,634 | 20,122 |
| % | 7.39 | 92.61 | 100 |

| | Presence of cancer cell | | |
|---|---|---|---|
| ID | No | Yes | Total |
| D | | | |
| Patient 7 | 71 | 5,622 | 5,693 |
| % | 1.25 | 98.75 | 100 |
| Patient 8 | 519 | 7,996 | 8,515 |
| % | 6.1 | 93.9 | 100 |

TABLE 5

Predictions of Logistic model based on all imaged cells.

| | Presence of cancer cell | | |
|---|---|---|---|
| ID | No | Yes | Total |
| A | | | |
| HPrEpiC | 1,674 | 392 | 2,066 |
| % | 81.03 | 18.97 | 100 |
| LNCaP | 159 | 17,278 | 17,437 |
| % | 0.91 | 99.09 | 100 |
| B | | | |
| Patient 5 | 6 | 11,579 | 11,585 |
| % | 0.05 | 99.95 | 100 |
| Patient Z | 704 | 7,811 | 8,515 |
| % | 8.27 | 91.73 | 100 |

| | Presence of cancer cell | | |
|---|---|---|---|
| Phase | No | Yes | Total |
| C | | | |
| B1 | 209 | 2,510 | 2,719 |
| % | 7.69 | 92.31 | 100 |
| P | 1,077 | 19,045 | 20,122 |
| % | 5.35 | 94.65 | 100 |

| | Presence of cancer cell | | |
|---|---|---|---|
| ID | No | Yes | Total |
| D | | | |
| Patient 7 | 96 | 5,597 | 5,693 |
| % | 1.69 | 98.31 | 100 |
| Patient 8 | 704 | 7,811 | 8,515 |
| % | 8.27 | 91.73 | 100 |

The second logistic regression model was developed using all imaged cells (139,165) from Patients 1 to 5 (development dataset, Table 4). The second logistic model had a cutoff point of 0.9, resulting in 85% sensitivity and specificity (FIG. 6). With the second logistic model 85% of cells were accurately classified (FIG. 6). The model identified 87% of the HPrEpiC as normal and in contrast 99% of the LNCaP cells as cancer-like (transformed, Table 5A). The two "supposedly benign" tissues were indicated to contain 100% (Patient 5) and 84% (Patient Z) aberrant cells (Table 5B). For Patient 6, 92% of cells in the initial biopsy and 95% of cells in prostatectomy samples were classified as aberrant cells (Table 5C). For Patient 7 the model estimated that 98% of cells isolated during first biopsy were cancer-like. The logistic model based on all cells estimated that 92% of the cells from Patient 8 being abnormal (Table 5D).

Modeling the Prediction of Indolent Versus Progressive Cancer

Towards the third goal of the study, the analyses focused on the prediction of a) the cancer stage (cancer type and localization), and b) cancer aggressiveness and disease progression. Cancer stage was defined by the six pathological categories: benign, atypical small acinar proliferation (ASAP), adenocarcinoma (AC), lots of adenocarcinoma (LAC), as diagnosed at biopsy, and stage II and stage III as diagnosed at prostatectomy. Cancer aggressiveness and disease progression were defined by four categories based on GS: benign (B) or no score (Group 1), score 6 (3+3) (Group 2), score 7 (3+4) (Group 3), and score 7 (4+3) (Group 4).

For the purpose of developing predictive models k-nearest neighbor (KNN) classifier, a machine-learning tool, was applied. Both, in development and validation, the same strategy (tissue data) was employed as for the logistic regression model: first only epithelial cells and subsequently subsets of random cells across all tissues categories (com-

TABLE 4

Logistic regression model coefficients or all cells.

Figure 7A:
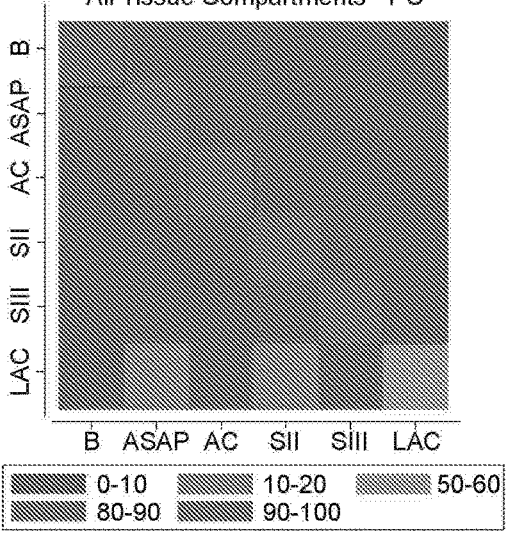
FIGS. 7A-7D depict, in accordance with various embodiments of the invention, heat maps representing the performance of the k-nearest neighbor (KNN) classification. SII=stage II, and SIII=stage III, PC=pathological categories.
Figure 7B:
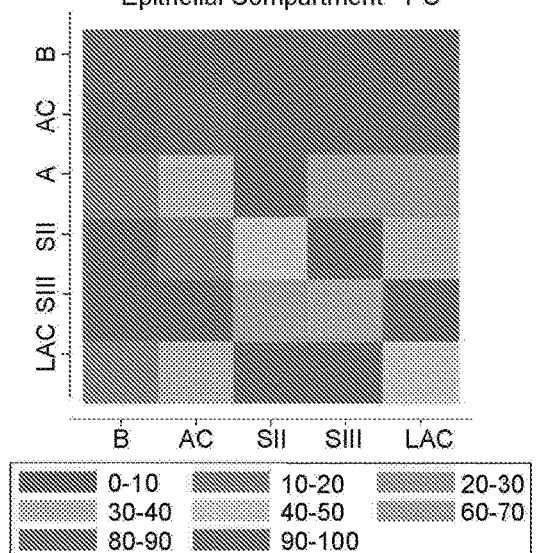
Figure 7C:
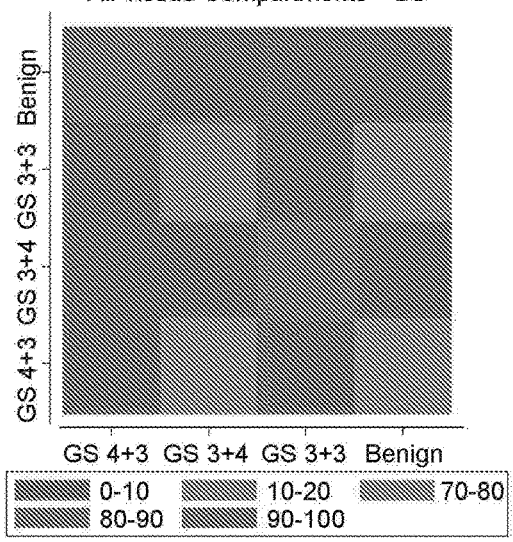
Figure 7D:
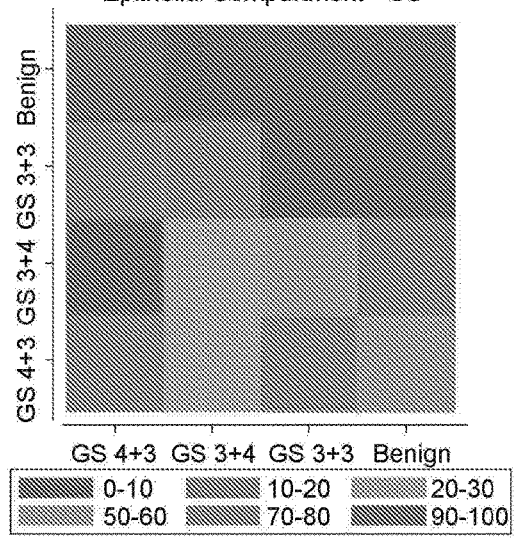
Figures 8A, 8B, 8C:
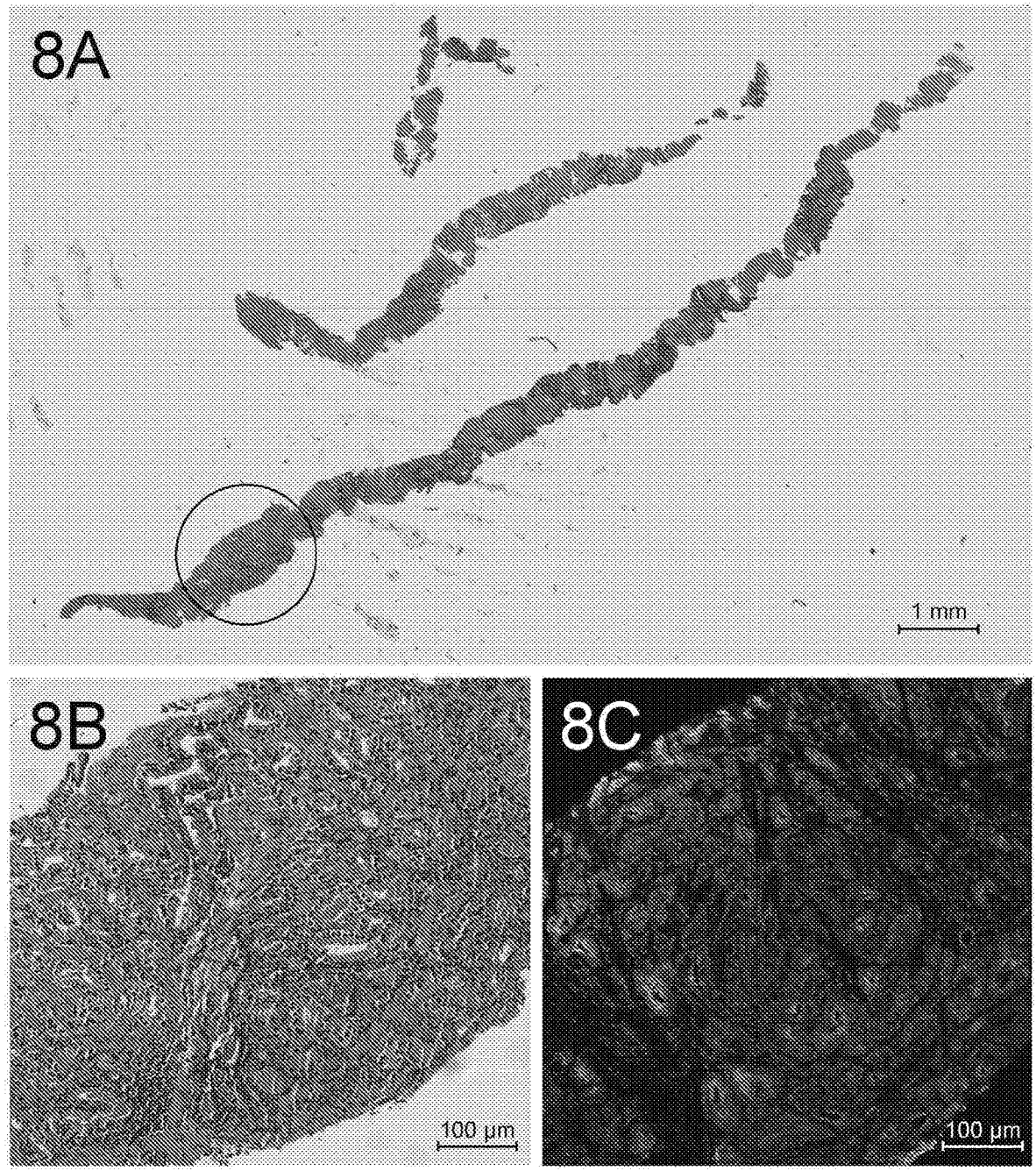

| Marker | Odds Ratio | Std. Err. | z | P > z | Conf. | [95% Interval] |
|---|---|---|---|---|---|---|
| lnDAPI | 6.459606 | 0.1339882 | 89.94 | <0.0001 | 6.20226 | 6.727629 |
| lnAMACR | 0.4555956 | 0.0120028 | −29.84 | <0.0001 | 0.4326676 | 0.4797386 |
| ln5mC | 0.0290629 | 0.0009604 | −107.08 | <0.0001 | 0.0272403 | 0.0310075 |
| ln5hmC | 3.055547 | 0.0929042 | 36.74 | <0.0001 | 2.878778 | 3.243171 |
| _cons | 3845.418 | 650.8334 | 48.77 | <0.0001 | 2759.806 | 5358.073 | partments) were recruited in order to generate two unique models per category scheme. For predictive modeling of cancer stages a total of 17,881 imaged epithelial cells were drafted. Of these, 3,829 cells were recruited from benign (per logistic regression analysis) tissue sources. The KNN classification identified 91% of these cells as benign or non-cancerous. 84% of the 11,712 cells in ASAP were correctly classified (FIGS. 7A-7D). Overall, the KNN was able to faithfully affiliate tissue stage with 67% accuracy (FIG. 7B).

Once the KNN classification was established model validation was pursued. Of the 2,066 HPrEpiC KNN identified 87% to be benign (Table 6A). Of the 17,437 LNCaP cells 62% were found to belong to stage II and 22% were classified as LAC-type cells. In the assumingly healthy prostatectomy-derived tissue from Patient 5, who had been diagnosed with stage III (pT3b) PCa, KNN affiliated the majority of cells (65%) to LAC, closely followed by 20% (on average) of stage III-type cells. For Patient Z the model classified 60% of the cells as LAC-type, followed by 28% classified to stage III (Table 6B). For Patient 6 it was estimated that from the 2,719 cells obtained during biopsy 39% and 29% were classified as stage III and LAC-type, respectively. Similarly, from the 20,122 cells isolated during prostatectomy, 51% were classified as stage III cancer and 43% as LAC-type (Table 6C). Finally, the majority of cells in Patients 7 (68%) and 8 (49%) were also classified as stage III-like cancer cells and 49% of the cells from Patient 8 were identified as stage III, followed by smaller portions of LAC-type cells: 17% and 22%, respectively (Table 6D).

To simplify the use of the KNN classification all the cells available were used without discrimination based on tissue (compartment) origin. One limitation of the KNN methodology is that it requires immense meta-data storage capabilities. Hence in order to make the development dataset more portable it was determined that 30,000 cells from both tissue compartments (epithelium and stroma) and across all six stage-related categories was the optimal number of cells that needed to be randomly chosen for obtaining the most accurate KNN classification. Even though either solely epithelial cells or a subset of all imaged cells (139,165 cells) were used for the development of the KNN classifications, model accuracy was assessed with all 139,165 cells from the development dataset (FIG. 7A). KNN failed to classify a marginal portion of 4% (~5.500 cells). From the remaining 96% of cells, KNN classification faithfully affiliated 79% of all imaged cells. In detail, the analysis of the validation dataset showed that 80% of the HPrEpiC were correctly identified as being normal (benign), and 87% of the LNCaP cells were classified as stage II cancer cells (Table 7A). The assumingly benign prostatectomy tissues isolated from PCa patients were indicated as follows: Patient 5 tissue was diagnosed of harboring 68% stage II cells followed by 24% LAC-type cells (Table 7B). Subject Z tissue was found to consist of 44% stage II cells and an almost equal portion (38%) of LAC cells. Further, for Patient 6, biopsy 1 was populated with a majority (45%) of LAC-type cells and an additional 19% of stage II cells. The prostatectomy tissue seemed to host a majority (47%) of LAC cells and a smaller fraction (37%) of stage II cells (Table 7C). Cells from

TABLE 6

KNN classification validation of cancer stages based on epithelial cells only predictions with Biomarkers I.

A Classification

| ID | B | ASAP | Stage II | Stage III | LAC | Total |
|---|---|---|---|---|---|---|
| HPrEpiC | 1,798 | 29 | 49 | 102 | 88 | 2,066 |
| % | 87.03 | 1.4 | 2.37 | 4.94 | 4.26 | 100 |
| LNCaP | 128 | 1,070 | 10,775 | 1,587 | 3,877 | 17,437 |
| % | 0.73 | 6.14 | 61.79 | 9.1 | 22.23 | 100 |

B Classification

| ID | B | ASAP | Stage II | Stage III | LAC | Total |
|---|---|---|---|---|---|---|
| Patient 5 | 2 | 61 | 1,687 | 2,355 | 7,480 | 11,585 |
| % | 0.02 | 0.53 | 14.56 | 20.33 | 64.57 | 100 |
| Patient Z | 207 | 832 | 73 | 2,652 | 5,610 | 9,374 |
| % | 2.21 | 8.88 | 0.78 | 28.29 | 59.85 | 100 |

C Classification

| Phase | B | ASAP | Stage II | Stage III | LAC | Total |
|---|---|---|---|---|---|---|
| B1 | 589 | 202 | 87 | 1,052 | 789 | 2,719 |
| % | 21.66 | 7.43 | 3.2 | 38.69 | 29.02 | 100 |
| P | 437 | 650 | 74 | 10,270 | 8,691 | 20,122 |
| % | 2.17 | 3.23 | 0.37 | 51.04 | 43.19 | 100 |

D Classification

| ID | B | ASAP | Stage II | Stage III | LAC | Total |
|---|---|---|---|---|---|---|
| Patient 7 | 9 | 250 | 536 | 3,851 | 983 | 5,629 |
| % | 0.16 | 4.44 | 9.52 | 68.41 | 17.46 | 100 |
| Patient 8 | 232 | 1,038 | 1,215 | 4,136 | 1,894 | 8,515 |
| % | 2.72 | 12.19 | 14.27 | 48.57 | 22.24 | 100 |

Patient 7's first biopsy—initially diagnosed with stage II (pT2c) adenocarcinoma—were classified to be 63% of LAC-type and 28% Stage II-type, with a minor Stage III component (7%). The patient had not progressed beyond this stage at prostatectomy (Table 1). In comparison, almost 38% and 29% of the cells from Patient 8's biopsy—initially diagnosed with stage II (pT2c) adenocarcinoma—were identified to be of LAC and stage II-type, respectively, with a larger stage III fraction (22%) (Table 7D). Also this patient had not progressed further at prostatectomy (Table 1).

(16%) (Table 8C). This trend seemed to be even more advanced at the time of prostatectomy (patient was diagnosed with GS (3+3)), where 41% of the 20,122 analyzed cells were classified as Group 3 and a larger portion (54%) as the more aggressive Group 4 cells. As for patient 7—initially diagnosed with adenocarcinoma GS (3+3)—the cells were almost equally classified into GS6 (40%) and GS (3+4) (44%) with a minor portion of GS (4+3) cells (15%) (Table 8D). At the time of prostatectomy the patient had not significantly progressed and had been diagnosed with GS

TABLE 7

KNN classification-based predictions of cancer stages with subsets of 30,000 cells and Biomarkers I.

A Classification

| ID | B | ASAP | AC | Stage II | Stage III | LAC | Total |
|---|---|---|---|---|---|---|---|
| HPrEpiC | 1,613 | 20 | 221 | 35 | 16 | 106 | 2,011 |
| % | 80.21 | 0.99 | 10.99 | 1.74 | 0.8 | 5.27 | 100 |
| LNCaP | 78 | 262 | 430 | 14,681 | 264 | 1,220 | 16,935 |
| % | 0.46 | 1.55 | 2.54 | 86.69 | 1.56 | 7.2 | 100 |

B Classification

| ID | B | ASAP | AC | Stage II | Stage III | LAC | Total |
|---|---|---|---|---|---|---|---|
| Patient 5 | 0 | 1 | 24 | 7,693 | 878 | 2,716 | 11,312 |
| % | 0 | 0.01 | 0.21 | 68.01 | 7.76 | 24.01 | 100 |
| Patient Z | 201 | 1,062 | 35 | 3,935 | 265 | 3,415 | 8,913 |
| % | 2.26 | 11.92 | 0.39 | 44.15 | 2.97 | 38.31 | 100 |

C Classification

| Phase | B | ASAP | AC | Stage II | Stage III | LAC | Total |
|---|---|---|---|---|---|---|---|
| B1 | 277 | 131 | 416 | 453 | 56 | 1,102 | 2,435 |
| % | 11.38 | 5.38 | 17.08 | 18.6 | 2.3 | 45.26 | 100 |
| P | 330 | 443 | 263 | 6,164 | 1,705 | 7,874 | 16,779 |
| % | 1.97 | 2.64 | 1.57 | 36.74 | 10.16 | 46.93 | 100 |

D Classification

| ID | B | ASAP | AC | Stage II | Stage III | LAC | Total |
|---|---|---|---|---|---|---|---|
| Patient 7 | 7 | 11 | 32 | 1,568 | 411 | 3,495 | 5,524 |
| % | 0.13 | 0.2 | 0.58 | 28.39 | 7.44 | 63.27 | 100 |
| Patient 8 | 142 | 140 | 578 | 2,291 | 1,779 | 2,968 | 7,898 |
| % | 1.8 | 1.77 | 7.32 | 29.01 | 22.52 | 37.58 | 100 |

The predictive power of the KNN algorithm considering GS was estimated using the same two subgroup data as for cancer stages: a) purely epithelial cells and b) subsets of 30,000 epithelial and stromal cells. For both approaches cells across all samples of Patients 1 to 5 were used (FIGS. 7A-7D). The KNN based exclusively on epithelial cells correctly classified 67% of cells in the development dataset (FIG. 7B). During validation it was determined that 88% of HPrEpiC were classified as benign/normal (Group 1), and the absolute majority of the LNCaP cells were identified as cancer cells: 67% were associated with the more advanced GS 7 (3+4) (Group 3) and 23% even with GS 7 (4+3) (Group 4), as shown in Table 8A. Again, KNN classified the supposedly healthy prostatectomy tissue from Patients 5 and Z to be populated with an absolute majority (72% and 68%, respectively) of the more aggressive Group 4 cells (Table 8B). For Patient 6—diagnosed with adenocarcinoma GS (3+3)—biopsied tissue was almost equally partitioned into 32% Group 3 cells and 29% Group 4 cells, followed by smaller portions of the Group 1 (23%) and Group 2 cells (3+3) in 40% of total tissue, however with perineural invasion present (Table 1). In the case of Patient 8 KNN classified the biopsied tissue to contain a majority (54%) of GS (3+4) cells closely followed by a large fraction (38%) of GS (3+3) cells. The patient was diagnosed with GS7 (3+4) at initial biopsy as well as later prostatectomy.

TABLE 8

KNN classification validation of GS based on epithelial cells only predictions with Biomarkers I.

| | Classification | | | | |
|---|---|---|---|---|---|
| ID | B | 3 + 3 | 3 + 4 | 4 + 3 | Total |
| A | | | | | |
| HPrEpiC | 1,820 | 27 | 140 | 79 | 2,066 |
| % | 88.09 | 1.31 | 6.78 | 3.82 | 100 |
| LNCaP | 154 | 1,535 | 11,697 | 4,051 | 17,437 |
| % | 0.88 | 8.8 | 67.08 | 23.23 | 100 |

TABLE 8-continued

KNN classification validation of GS based on epithelial cells only predictions with Biomarkers I.

| | B | | | | |
|---|---|---|---|---|---|
| Patient 5 | 4 | 49 | 3,234 | 8,298 | 11,585 |
| % | 0.03 | 0.42 | 27.92 | 71.63 | 100 |
| Patient Z | 210 | 679 | 2,113 | 6,372 | 9,374 |
| % | 2.24 | 7.24 | 22.54 | 67.98 | 100 |

| | Classification | | | | |
|---|---|---|---|---|---|
| Phase | B | 3 + 3 | 3 + 4 | 4 + 3 | Total |
| | | | C | | |
| B1 | 638 | 441 | 865 | 775 | 2,719 |
| % | 23.46 | 16.22 | 31.81 | 28.5 | 100 |
| P | 420 | 554 | 8,239 | 10,909 | 20,122 |
| % | 2.09 | 2.75 | 40.95 | 54.21 | 100 |

| | Classification | | | | |
|---|---|---|---|---|---|
| ID | B | 3 + 3 | 3 + 4 | 4 + 3 | Total |
| | | | D | | |
| Patient 7 | 8 | 2,226 | 2,516 | 879 | 5,629 |
| % | 0.14 | 39.55 | 44.7 | 15.62 | 100 |
| Patient 8 | 239 | 3,278 | 4,584 | 414 | 8,515 |
| % | 2.81 | 38.5 | 53.83 | 4.86 | 100 |

The performance of the KNN classification using randomly selected subsets of 30,000 cells was on average 79% accurate within the development set of 139,165 cells (FIG. 7C). 81% of the HPrEpiC were found to be non-cancerous (Group 1), and conversely 77% of the LNCaP cells were assigned to Group 3 (Table 9A). The supposedly benign prostatectomy tissue of Patient 5 harbored 55% Group 3 cells and 45% Group 4 cells. For Patient Z the associations were reciprocal: 52% Group 4 and 37% to Group 3 cells (Table 9B). Lastly, for Patient 6 biopsy 1 showed a larger number (59%) of Group 4 cells. This portion increased to 69% at prostatectomy (Table 9C). The majority of cells from Patient 7 (67%) and Patient 8 (48%) were found to be of Group 4-type (GS (4+3)) closely followed by Group 3 cells (Patient 8: 30%; Patient 9: 36%; Table 9D).

TABLE 9

KNN classification-based predictions of GS with subsets of 30,000 cells and Biomarkers I.

| | Classification | | | | |
|---|---|---|---|---|---|
| ID | B | 3 + 3 | 3 + 4 | 4 + 3 | Total |
| | | | A | | |
| HPrEpiC | 1,672 | 166 | 33 | 195 | 2,066 |
| % | 80.93 | 8.03 | 1.6 | 9.44 | 100 |
| LNCaP | 85 | 507 | 13,482 | 3,363 | 17,437 |
| % | 0.49 | 2.91 | 77.32 | 19.29 | 100 |
| | | | B | | |
| Patient 5 | 0 | 67 | 6,323 | 5,195 | 11,585 |
| % | 0 | 0.58 | 54.58 | 44.84 | 100 |
| Patient Z | 222 | 792 | 3,500 | 4,860 | 9,374 |
| % | 2.37 | 8.45 | 37.34 | 51.85 | 100 |

TABLE 9-continued

KNN classification-based predictions of GS with subsets of 30,000 cells and Biomarkers I.

| | Classification | | | | |
|---|---|---|---|---|---|
| Phase | B | 3 + 3 | 3 + 4 | 4 + 3 | Total |
| | | | C | | |
| B1 | 254 | 329 | 539 | 1,597 | 2,719 |
| % | 9.34 | 12.1 | 19.82 | 58.73 | 100 |
| P | 344 | 537 | 5,349 | 13,892 | 20,122 |
| % | 1.71 | 2.67 | 26.58 | 69.04 | 100 |

| | Classification | | | | |
|---|---|---|---|---|---|
| ID | B | 3 + 3 | 3 + 4 | 4 + 3 | Total |
| | | | D | | |
| Patient 7 | 13 | 117 | 1,705 | 3,794 | 5,629 |
| % | 0.23 | 2.08 | 30.29 | 67.4 | 100 |
| Patient 8 | 183 | 1,176 | 3,086 | 4,070 | 8,515 |
| % | 2.15 | 13.81 | 36.24 | 47.8 | 100 |

With Biomarkers II the identical approach to the first panel was taken. Briefly, the channel values for all markers had to be log-transformed because the data did not show a normal distribution. Logistic regression analysis was then conducted in order to predict the specificity and sensitivity of the second panel for successful prediction of presence or absence of aberrant cells in a subset of all imaged cells. Then the model was applied to the same training dataset. When considering only epithelial cells in the analysis with the second panel, unfortunately data was missing for several cancer stages. Only stage II-type, stage III-type and benign cells were present. Nevertheless, the model was able to achieve a fairly good sensitivity (84%) and specificity (81%) over the quota of all 153,000 imaged cells. However, the model trained with Biomarkers II failed to identify HPrEpiC as benign. Instead it characterized 98% of these primary cells as being malignant. This was also the case when all imaged cells (from all tissues of Patients 1 to 5) were used for model development. As abovementioned, since for Biomarkers II there were only 3 tissue categories available when using cells from the epithelial compartment for model development, KNN was applied with cells from all tissue compartments. While almost 100% accuracy was obtained in correctly matching the cells with their respective stage, the KNN classification developed with Biomarkers II also failed to identify the majority of HPrEpiC as benign. Instead, 64% of HPrEpiC were classified as stage III-type cancer cells while only 22% were faithfully classified as benign. Hence the further assessment of Biomarkers II was not pursued.

Discussion

The aims of the study were to assess the potential of two sets of biomarkers in conjunction with 3D high-content imaging and fluorescence readout towards: a) early detection of aberrant cells in prostatic tissue using logistic regression analysis, and b) consequently prediction of cancer progression based on cell composition in biopsied tissue at first diagnosis, powered by KNN classification. The novelty of this study was two-fold: (i) in the combinatorial use of global epigenetic features (DNA methylation/hydroxymethylation and histone-tail modifications) together with established markers of prostate pathology, and (ii) the application of extracted single-cell information for diagnostic/prognostic disease modeling. Through principal component analysis it was established that Biomarkers I including 5mC and 5hmC presented a better partitioning of the data (FIGS. 3A-3B) and showed a better performance (specificity/sensitivity) in both cases when pathological categories and GS where used as reference pathological tissue classifications. Therefore, data analysis of Biomarkers I was determined to be an appropriate choice.

Both logistic regression and KNN classifiers employed in the study had been previously applied for the purpose of early detection of cancer. However, in those studies both methods have been either used to cross-validate the approaches or compared against each other to assess their respective predictive performance. Perhaps the most challenging aspect of the previous analyses had been narrowing down the number of predictors since KNN classifier only performs well with a very limited number of independent variables. In the present study, the two sets of biomarkers were chosen in part based on scientific rationale and in part based on clinical validation for a majority of cancers and especially for PCa (as referenced above) rather than their statistical performance.

Statistical Methods

The statistical methodology presented here differs from previously reported applications in at least two aspects. First, rather than using the two approaches for cross-validation, logistic regression was used to characterize the composition of cells which would be indicative of the presence or absence of PCa-specific aberrations using logistic regression. Subsequently, KNN classifier was utilized to correlate these aberrations with stage/grade of cancer. Thus, the two approaches operated collectively in the prediction of PCa presence and severity. Second and final, in the above-mentioned previous studies, each observation had been relating to one patient sample, whereas in the present case each observation was related to a single cell within a tissue sample.

Thus, the inventive approach is a true cell-by-cell approach and the derived model predicts the presence or absence of aberrant cancer-like cells, leading to the characterization of the overall tissue sample based on its composition of classified cells and the resulting portion of aberrant cells. Hence a more detailed profile of a patient sample with a probabilistic outcome that may allow for prediction of cancer progression (prognostics) was established, rather than only generating a diagnostic snapshot. From a data-structure perspective, in the first stage of analysis, logistic regression was used, which implied a binary outcome—presence (value 0) or absence (value 1) of malignancy—for each cell. In the second and final step of the analysis, there was a shift towards a polychotomous outcome by which either the resulting cancer stage or cancer grade was predicted based on the proportions of the different categories of cells. As part of the comprehensive statistical analyses and in order to determine whether the chosen marker panels serve as good predictors of prostate cancer stage and grade, it was demonstrated that Biomarkers I were able to distinguish between benign and aberrant cells. Towards that two logistic models were developed. The first one was based on the recruit of solely epithelial cells from a set of five patients to predict the likelihood of cancer, followed by a second logistic model for which all the cells in our model-development dataset, i.e. additionally stroma-located cells were employed. Based on the estimates of the coefficients of the logistic model (Tables 2 and 4), it became clear that all of the four markers (DAPI, AMACR, 5mC and 5hmC) were significantly associated with the likelihood of cancer. Furthermore, the panel revealed excellent sensitivity and specificity scores as also presented by AUROCs of the data used for the development of the model (FIG. 6).

Detection of Benign and Aberrant Cells in Benign Prostate Tissue

In the first step, the goal was to assess whether prostate tissue isolated from a patient diagnosed to have PCa and classified as "normal" by an expert pathologist, would contain aberrant cells. By that the goal was to establish if Biomarkers I would indicate any signatures of malignancy present in a tissue that was labeled as benign according to conventional pathological features. Not only were aberrant cells detected in these "benign" validation samples but these aberrant cells were accurately correlated with stage and GS of the patients' tumors. It is worth noting that while these benign samples were not included in the development datasets, other malignant tissue from the same patients was. This fact underlines the capability of single-cell characterization with Biomarkers I of identifying already existing cancer-like aberrations in occult tissue beyond the tumor region. This feature would be in agreement with the concept of field cancerization, also known as a field effect or field defect, which suggests that detectable epigenetic alterations occur in histopathologically nonmalignant tissue that is contiguous with cancerous tissue. Epigenetic changes in field cancerization not only involve hypermethylation, but also hypomethylation. Because the field in which altered cells reside can extend beyond the morphologically evident tumor into the tumor environment, current histopathological practices may result in high false-negative diagnoses. However, with the implementation of epigenetic biomarkers there is hope to improve this aspect: biopsy samples taken from outside the cancerous tumor focus that result in negative pathology findings with current practices may produce a positive diagnostic result when epigenetic features are included into tissue analysis and classification. This may also reduce the burden of repeat biopsies. Within this context, the novel approach with Biomarkers I could potentially raise the chance of detecting malignancy even if neoplastic tissue (as per current definition) is being missed during needle biopsy (currently in 20-30% of cases). This would lead to decreasing the chance of false-negative calls, thus speaking in favor of a better early PCa diagnosis.

Validation and Prediction of Cancer Grading using Known Cell Culture Models

Unfortunately, for a direct comparison of malignant versus benign tissue, a more reliable normal reference tissue was not obtained, i.e. prostate tissue samples from patients that were not diagnosed as having PCa or any other malignancy in follow-up examinations. Therefore, in the second step the focus was on using well-established and comprehensively analyzed cell cultures for comparative validation: LNCaP cells as a positive control and primary HPrEpiC representing normal non-transformed cells of epithelial origin. Again, the inventive classification methods accurately identified HPrEpiC and LNCaP cells to be normal and aberrant, respectively, with highest probabilities (90% and 99%).

Validation and Prediction of Cancer Progression

In step three of the validation an equally important matter was assessed, i.e. the capability of the single-cell imaging approach with Biomarkers I to predict tissue/cancer progression with data obtained at initial biopsy and projected towards prostatectomy. Also in this regard both classifications were able to correctly predict PCa indolence in all three validation Patients 6, 7, and 8 down to stage and GS, as no change was reported for either specification at later prostatectomy. In summary, both mathematical-statistical classification methods demonstrated excellent predictive capabilities in conjunction with cancer staging, whereas KNN resting on GS revealed mixed scores that were not presented by pathological (expert) test results.

The latter needs to be further investigated, whether these results could reflect or explain the current controversies in the field of Gleason scoring. With the advent of thin core biopsy and radical prostatectomy it has become clear that, as originally defined, some aspects of the GS system do not accord with subsequent clinical behavior. Even though the system has been subject to changes since 2005, areas of controversy remain regarding GS6 and in particular GS7. Donald Gleason himself noted exact reproducibility of score in 50% of needle biopsies and a variance of ±1 score in 85%, similar to the findings of others. Finally, and critical in terms of practicality, it was determined that the performance of Biomarkers I-based models using randomized groups of cells across all tissue compartments (including epithelium and stroma) for cell-by-cell classification of tissues are independent from the location of the analyzed cells. Thus the approach resulted in a huge technical benefit as it does not require highly challenging and tedious steps of post-imaging tissue demarcation and particular computational selection of epithelial cells for analysis.

It was determined that tissue characterization by single-cell 3D high-content analysis using Biomarkers I (DAPI, 5mC, 5hmC and AMACR) showed favorable predictive values when combined with the two types of statistical learning methods: a) the logistic model to predict composition of aberrant versus benign cells in tissue samples, and b) KNN classification to correlate cell composition with cancer staging and grading for prediction of cancer progression at first diagnosis.

Materials and Methods

Cultured Cells and Tissues

Cultured cells included primary human prostate epithelial cells (HPrEpiC, ScienCell, Carlsbad, CA), and the LNCaP cancer cell line (American Type Culture Collection, Manassas, VA). For this study HPrEpiC at an early passage were used to rule out a decrease in global DNA methylation due to proliferative aging in culture, which is typical for primary cells and especially for these cells. Cells were cultured at 37° C. and 5% $CO_2$ following standard culture procedures as previously described.

For the purpose of this analysis de-identified archived tissues from eight PCa patients were used and two well-characterized human cell lines of prostatic origin: human prostate epithelial cells (HPrEpiC) as normal primary cells at early stage in culture, and LNCaP, an androgen-sensitive prostate cancer cell line. For each patient tissues taken at different diagnostic time points were analyzed, including diagnosis—first biopsy (biopsy 1) and if available second biopsy (biopsy 2)—and paired prostatectomy.

Immunofluorescence

Tissue sections were deparaffinized, fixed with 4% paraformaldehyde/phosphate buffered saline, and subjected to antigen-retrieval using Target Retrieval Solution (Dako, Carpinteria, CA) according to the manufacturer's protocol, all prior to labeling procedures. Immunofluorescence for cells and tissues was performed according to previously established protocols (See Tajbakhsh J. Covisualization of methylcytosine, global DNA and protein biomarkers for in situ 3-D DNA methylation phenotyping of stem cells. Methods Mol Biol. 1052:1-12.; Tajbakhsh J., Wawrowsky K. Using 3D high-content analysis and epigenetic phenotyping of cells in the characterization of human prostate tissue heterogeneity. Single Cell Biol 2015; 4:1, 1000i104). Unconjugated primary antibodies used were: monoclonal mouse anti-5-methylcytosine clone 33D3 (Aviva Systems Biology), polyclonal rabbit anti-5-hydroxymethylcytosine (Active Motif), polyclonal sheep anti-AMACR (R&D Systems), polyclonal goat anti-SAFB (Santa Cruz Biotechnology), polyclonal rabbit anti-H3K9me3 (Active Motif), monoclonal mouse anti-H3K27me3 (Active Motif), and monoclonal rat anti-AR (Santa Cruz Biotechnology). Matching secondary antibodies (all from Life Technologies, now Thermo Fisher Scientific) included: Alexa 488-conjugated donkey anti-mouse IgG (H+L), Alexa 555-conjugated donkey anti-sheep IgG (H+L); Alexa 555-conjugated donkey anti-goat IgG (H+L), Alexa 594-conjugated goat anti-rabbit IgG (H+L), Alexa 647-conjugated chicken anti-rabbit IgG (H+L), Alexa 647-conjugated donkey anti-sheep IgG (H+L), and Alexa 680-conjugated goat anti-rat IgG (H+L). The specimens were counterstained with 4',6-diamidino-2-phenylindole (DAPI), prior to embedding in ProLong Gold (Thermo Fisher Scientific).

In another example, in order to preserve the three-dimensional structure, cells cultured on glass coverslips in 12-well microplates (Costar, Corning) were fixed with 4% paraformaldehyde/phosphate buffered saline (PBS) (Sigma-Aldrich) and processed for immunofluorescence as previously described [64]. The following antibody sets were used: a monoclonal mouse anti-5-MeC antibody (Clone 33D3, Aviva Systems Biology, San Diego, CA) together with an Alexa488-conjugated polyclonal donkey anti-mouse IgG (H +L) (Invitrogen), and a polyclonal rabbit anti-H3K9me3 antibody (Active Motif) together with an Alexa647-conjugated chicken anti-rabbit IgG (H +L) (Invitrogen). All specimens were counterstained with DAPI.

Image Acquisition and Analysis

Confocal imaging of labeled cells and tissues was performed as previously described in Tajbakhsh J, Wawrowsky K. Using 3D high-content analysis and epigenetic phenotyping of cells in the characterization of human prostate tissue heterogeneity. Single Cell boil 2015; 4:1, 1000i104, the content of which is incorporated herein by reference in its entirety. To avoid bleed channel bleed through due to overlap of emission spectra, images were acquired serially: first DAPI, Alexa 555, and Alexa 647 dyes, followed by Alexa 488 and Alexa 594. 3D image analysis was performed as described in Gertych A, Wawrowsky K A, Lindsley E, Vishnevsky E, Farkas D L, Tajbakhsh J. Automated quantification of DNA demethylation effects in cells via 3D mapping of nuclear signatures and population homogeneity assessment. Cytometry A 2009; 75: 569-83; Oh J H, Gertych A, Tajbakhsh J. Nuclear DNA methylation and chromatin condensation phenotypes are distinct between normally proliferating/aging, rapidly growing/immortal, and senescent cells. Oncotarget. 2013; 4: 474-93; and Tajbakhsh J, Stefanovski D, Tang G, Wawrowsky K, Liu N, Fair J H. Dynamic heterogeneity of DNA methylation and hydroxymethylation in embryonic stem cell populations captured by single-cell 3D high-content analysis. Exp Cell Res. 2015; 332: 190-201.

The resulting dat-files were incorporated into software for statistical analysis, as described in the following section.

In some examples, specimens were imaged by a confocal laser-scanning microscope (TCS SP5 X Supercontinuum, Leica Microsystems Inc.) that allows for any excitation line within the continuous range of 470 to 670 nm, in 1 nm increments. The system was additionally equipped with a 405 nm diode laser line for excitation of fluorescence. Serial optical sections were collected at increments of 200-300 nm with a Plan-Apo 63× 1.3 glycerol immersion lens (pinhole size was 1.0 Airy unit). To avoid bleed-through, the imaging of each channel was performed sequentially. The typical image size was 2048×2048, with a respective voxel size of 116 nm×116 nm×230.5 nm (x, y, and z axes), and resolution was 12 bits per pixel in all channels. Fluorescence intensity of the desired methylation or other signals from optical two-dimensional sections were recorded into separate 3D channels. Raw images were obtained as Leica Image Format (lif) and offline-converted to a series of TIFFs for downstream image analysis.

3D Image Analysis

In some examples, image analysis could be performed with three steps: 1) image segmentation resulting in the delineation of a 3D shell for each individual nucleus; 2) extraction of the desired epigenetic characteristics (e.g. 5mC) using signal intensity distributions within each 3D shell; 3) assessment of cell population heterogeneity through 2D histograms of MeC versus DAPI distribution patterns, utilizing K-L divergence, and 4) the mapping of LIMs and LIDs within individual nuclei.

In some example, one could calculate mean intensity of MeC signals. Images in each two-channel 3D stack were acquired under nearly identical conditions and modality settings, and so the drift of the settings during acquisition is considered minimal and can be neglected. For co-distribution analysis, the desired epigenetic signals maybe mapped as respective 2D scatter plots, and following [43] the Kullback-Leibler (KL) divergences were calculated between individual 2D plots (nuclei) and the reference 2D plot (cumulative plot from all nuclei in one drug/concentration experiment). Based on the KL value, cells were categorized as: similar KLG $\in$ [0, 0.5), likely similar KLG $\in$ [0.5, 2), unlikely similar KLG $\in$[[2, 4.5), and dissimilar KLG $\in$ [4.5, in order to evaluate a ratio of similar and dissimilar cells. For localization of resulting LIM and LID sites, the nuclei were analyzed by an algorithm introduced in [44]. Briefly, segmented nuclei were eroded at a constant voxel rate of 1.32 µm×1.3 µm×0.25 µm, and the epigenetic signals can be recorded as integrated intensity values within each nuclear shell. Then, local densities of sites as well and profiles were determined for each nuclear shell as the subset of voxels within a defined intensity range between two thresholds measured separately for each channel: tbcg is the threshold value for the background, and tQ, which separates high-amplitude from low-amplitude intensities. All analytical findings related to image processing including numerical results, co-distribution patterns, individual and combined images, outputs of cells were exported by means of a graphical user interface to text or graphics files respectively for further statistical analyzes. A built-in pseudo-coloring of divergence, and site shading was superimposed onto original images to facilitate visual reading and evaluation of experimental data.

FIG. 9 illustrates an example of a method for processing of 3D images accordingly the present disclosure. For instance, the method may include the step of outputting a 3D image of stained tissue, 3-D nuclei segmentation 905 of those 3D images, signal extraction of desired proteinaceous and nucleic acid components of the cell 910, pattern analysis of the desired components of each individual nuclei 920, characterization of each individual cell as normal (benign) or cancerous and enumeration of the two cell types 930, and output of a diagnosis or classification of the tissue 940. In some examples, the fluorescence intensity for different features from optical sections would be recorded into separate channels and measured in 3D. For instance, in this example, the fluorescence intensity for each of the following features (different staining for each feature) would be separated into these four different channels for Biomarkers I and measured in 3D: (1) DAPI, (2) AMACR, (3) 5mC, and (4) 5hmC.

In some examples, the pattern analysis will be performed by grouping nuclei based on the extracted components (e.g. intensity of fluorescence for each component), and drawing correlations to output a diagnosis or severity in some cases of the tested tissue. For instance, in some examples, logistic regression will identify and enumerate normal and cancer cells (composition of these two cell types 930)C, and KNN will output a pathological category or tumor grade (GS). Thus, step 930 may identify the amount of cancer cells, while step 940 will provide a more defined clinical diagnosis. A detailed example of how the steps 900 -920 in FIG. 9 can be performed are found on pages 572-577 of Gerytch, et al., "Automated Quantification of DNA Demethylation Effects in Cells via 3D Mapping of Nuclear Signatures and Population Homogeneity Assessment" 2009, the content of which is incorporated herein by reference. Additionally, the content of the entire publication Gerytch, et al., "Automated Quantification of DNA Demethylation Effects in Cells via 3D Mapping of Nuclear Signatures and Population Homogeneity Assessment" 2009, is incorporated herein by reference in its entirety. A detailed example of how the steps 930 and 940 in FIG. 9 can be performed are found on pages 57284-57298 of Stefanovski, et al., "Prostate cancer diagnosis using epigenetic biomarkers, 3D high-content imaging and probabilistic cell-by-cell classifiers" 2017, the content of which is incorporated herein by reference. See also, Stefanovski D., et al. Prostate cancer diagnosis using epigenetic biomarkers, 3D high-content imaging and probabilistic cell-by-cell classifiers. Oncotarget 2017 Jul. 5; 8(34): 57278, which is hereby incorporated by reference.

Mathematical-Statistical Modeling

In one example, analysis was conducted with STATA 14 (StataCorp., College Station, TX). Two statistical analyses were considered to answer the aims of the study. First, the focus was on the development of a logistic model that would determine the probability of a cell being non-cancerous (normal, benign) or cancerous (malignant, transformed), based on two separate sets of four Biomarkers I (DAPI, 5mC, 5hmC, AMACR) and five Biomarkers II (DAPI, SAFB, H3K9me3, H3K27me3, AR). A set of five subjects that were diagnosed with PCa was used at the time of biopsy or prostatectomy as the development dataset. The logistic analysis was performed once only with the cells located in the epithelial tissue compartment and then repeated once with all imaged cells from all tissue compartments (including the epithelial compartment). All data were analyzed in a cell-by-cell manner. In other words, for each cell the logistic model estimated a probability of being aberrant (cancerous, malignant) or normal (non-cancerous). Subsequently through assessment of assay sensitivity and specificity an optimal overall cutoff probability of cell malignancy was determined. The cells were classified as cancerous if the probability of cancer was equal to or above the cutoff probability or non-cancerous if the cells probability was below the cutoff level. Finally, tissues/samples were classified as non-cancerous or cancerous based on the category of their largest component of cells.

Second and final, two k-nearest neighbor (KNN) classifier were performed that would predict the two types of classifications of cells. KNN is a memory-based classifier and a model free approach (See The Elements of Statistical Learning. Data Mining, Inference, and Prediction, Second Edition.

Authors: Hastie, Trevor, Tibshirani, Robert, Friedman, Jerome. Springer New York.), the content of which is incorporated by reference herein in its entirety. For given cells and based on the intensities of the four markers, a shortest "distance" is calculated to the N-nearest neighbors. Based on the majority within these N-neighbors the classification is determined.

Despite its simplicity, KNN classification has been very successful in a large number of applications that originally faced classification challenges, such as satellite image scenes and EKG (See Bluemn EG, Nelson PS. The androgen/androgen receptor axis in prostate cancer. Curr Opin Oncol. 2012; 24: 251-7). The size of the cluster of nearest neighbors (k parameter) for the KNN classification was determined using the training data thereby maximizing the likelihood of correct classification (See Ghosh A K. On optimum choice of k in nearest neighbor classification. Computational Statistics & Data Analysis. 2006; 50: 3113-3123). It was determined that the best results were obtained with k=5. Thus, k was sufficiently large to diminish noise effects in the data, yet small enough to reduce computational expenses. Instead of Euclidian distance between the neighbors, Mahalanobis distance (See Mahalanobis P C. On the generalized distance in statistics. Proc Nat Inst Scien India 1936; 2: 49-55.) was used. The first classification was based on cancer stage at diagnoses (biopsies) and prostatectomy. The second version was considering GS (cancer grading) of the same specimens as an indicator of disease progression and cancer aggressiveness. The KNN classifications were developed using same development and validation datasets as for the logistic regression model. Hence analogously tissues were classified based on the category of the largest portion of cells.

Supplementary Data

TABLE 10

Principal components (eigenvectors) = Loading Matrix of Biomarkers I for epithelial compartment only.

| Variable | Comp1 | Comp2 | Unexplained |
|---|---|---|---|
| DAPI | −0.23 | 0.96 | 0.01 |
| AMACR | 0.60 | 0.13 | 0.20 |
| 5mC | 0.42 | 0.23 | 0.57 |
| 5hmC | 0.64 | 0.08 | 0.12 |

TABLE 11

Principal components (eigenvectors) = Loading Matrix of Biomarkers II for epithelial compartment only.

| Variable | Comp1 | Comp2 | Unexplained |
|---|---|---|---|
| DAPI | 0.15 | 0.75 | 0.32 |
| nAR | 0.56 | 0.22 | 0.11 |
| SAFE | 0.46 | −0.48 | 0.18 |
| H3K9me3 | 0.33 | 0.33 | 0.59 |
| H3K27me3 | 0.58 | −0.22 | 0.06 |

Selected Embodiments

Although the above description and the attached claims disclose a number of embodiments of the present invention, other alternative aspects of the invention are disclosed in the following further embodiments.

Embodiment 1. A method for determining if one or more prostate cells of a prostate tissue sample are cancerous or noncancerous; the method comprising:

quantifying one or more biomarkers in the one or more prostate cells, wherein the one or more biomarkers are selected from the group consisting of: global DNA (gDNA), 5-methylcytosine (5mC), 5-hydroxymethlcytosine (5hmC), and alpha-methylacyl-CoA racemase (AMCR, p504s); and determining if one or more of the prostate cells are cancerous or non-cancerous, based on the quantity of one or more of the biomarkers relative to cancerous and/or noncancerous cells, wherein a significantly higher quantity of gDNA and/or AMCR and/or a significantly lower quantity of 5mC and/or 5hmC, relative to non-cancerous cells, is indicative of prostate cancer.

Embodiment 2. The method of embodiment 1, further comprising utilizing a logistic regression (LR) model to predict a composition of aberrant versus benign cells in the prostate tissue sample.

Embodiment 3. The method of embodiment 2, wherein the aberrant cells are within a section of the prostate tissue sample that has been previously designated as benign by standard tissue pathology.

Embodiment 4. The method of embodiment 1, further comprising utilizing a k-nearest neighbor (KNN) classification to (1) correlate the prostate tissue cell composition with cancer staging and/or grading of cancer progression, and (2) predict how tissue stage and grade would be upon subsequent prostatectomy.

Embodiment 5. The method of embodiment 4, wherein the prostate tissue is obtained from a biopsy.

Embodiment 6. The method of embodiment 1, wherein the quantity of 5mC in one or more of the prostate cells is determined by high-resolution light microscopy in conjunction with computer-assisted image analysis after one or more of the prostate cells have been subjected to immunofluorescence staining with an antibody specific for 5mC.

Embodiment 7. The method of embodiment 1, wherein the quantity of 5hmC in one or more of the prostate cells is determined by high-resolution light microscopy in conjunction with computer-assisted image analysis after one or more of the prostate cells have been subjected to immunofluorescence staining with an antibody specific for 5hmC.

Embodiment 8. The method of embodiment 1, wherein the quantity of AMACR in one or more of the prostate cells is determined by high-resolution light microscopy in conjunction with computer-assisted image analysis after one or more of the prostate cells have been subjected to immunofluorescence staining with an antibody specific for AMACR.

Embodiment 9. The method of embodiment 1, wherein the quantity of gDNA in one or more of the prostate cells is determined by high-resolution light microscopy in conjunction with computer-assisted image analysis after one or more of the prostate cells have been treated with 6-diamidino-2-phenylindole (DAPI).

Embodiment 10. The method of embodiment 9, wherein the microscope is a confocal scanning microscope with a resolution equal to or less than one micrometer.

Embodiment 11. A method, comprising:

obtaining a sample of prostate tissue from a subject, wherein the prostate tissue comprises a prostate cell; and determining if one or more cells of the prostate tissue is cancerous or benign by employing the method of any one of embodiments 1-10.

Embodiment 12. A non-transitory machine readable medium having stored thereon instructions for performing a method comprising machine executable code which when executed by at least one machine, causes the machine to:

Embodiment 13. A system comprising:
- a light microscope;
- a computing device comprising:
  - a display;
  - a memory containing machine readable medium comprising machine executable code having stored thereon instructions;
  - a control system coupled to the memory comprising one or more processors, processors, the control system configured to execute the machine executable code to cause the one or more processors to:
    - receive 3D image data output from the microscope comprising fluorescent intensity data for a plurality of cells with a plurality of nuclei;
    - segment the 3D image data to identify a 3D shell for each individual nucleus of the plurality of nuclei;
    - extract a measure of signal intensity for at least two separate features within each 3D shell, wherein the signal intensity for each of the at least two separate features is extracted separately;
    - classify each cell with a status related to cancer based on the extracted measures of signal intensity for the at least two separate features; and
    - output the results on the display.

Embodiment 14. The system of embodiment 13, wherein the step of classifying each cell with the status related to cancer further comprises determining whether each cell is cancerous using a logistic regression model.

Embodiment 15. The system of embodiment 13, wherein the step of classifying each cell with the status related to cancer further comprises classifying a stage of cancer of the plurality of cells using a KNN classifier.

Embodiment 16. The system of embodiment 13, wherein the at least two separate features comprise the following biomarkers: global DNA (gDNA), 5-methylcytosine (5mC), 5-hydroxymethlcytosine (5hmC), and alpha-methylacyl-CoA racemase (AMCR, p504s).

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks.

However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

Conclusions

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context.

The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein.

Accordingly, many embodiments of this application include all modifications and equivalents of the subject matter recited in the claims appended hereto as permitted by applicable law. Moreover, any combination of the above-described elements in all possible variations is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method, comprising:
    obtaining a prostate tissue sample from a prostate of a human subject;
    quantifying four biomarkers in one or more prostate cells of the prostate tissue sample, wherein the four biomarkers are global DNA (gDNA), 5-methylcytosine (5mC), 5-hydroxymethylcytosine (5hmC), and alpha-methylacyl-CoA racemase (AMACR);
    determining if the one or more prostate cells are cancerous or non-cancerous, based on a quantity of the four biomarkers relative to cancerous and/or noncancerous cells, wherein a significantly higher quantity of gDNA and AMACR and a significantly lower quantity of 5mC and 5hmC, relative to non-cancerous cells, is indicative of presence of one or more cancerous prostate cells in the prostate tissue sample;
    classifying the one or more cancerous prostate cells according to cancer grade (Gleason score) and cancer stage in the one or more cancerous prostate cells;
    determining proportions of cancer grades (Gleason scores) and cancer stages in the prostate tissue sample based on a composition of the classified one or more cancerous prostate cells in the prostate tissue sample;
    classifying the prostate tissue sample according to the proportions of cancer grades (Gleason scores) and cancer stages in the prostate tissue sample; and
    predicting cancer progression in the prostate of the human subject based on the cancer grade (Gleason score) and the cancer stage in the one or more cancerous prostate cells.

2. The method of claim 1, further comprising utilizing a logistic regression (LR) model to predict a composition of aberrant versus benign cells in the prostate tissue sample.

3. The method of claim 2, wherein the aberrant cells are within a section of the prostate tissue sample that has been previously designated as benign by standard tissue pathology.

4. The method of claim 1, wherein the prostate tissue sample is obtained from a biopsy or prostatectomy.

5. The method of claim 1, wherein the quantity of 5mC in the one or more prostate cells is determined by high-resolution light microscopy in conjunction with computer-assisted image analysis after the one or more prostate cells have been subjected to immunofluorescence staining with an antibody specific for 5mC.

6. The method of claim 1, wherein the quantity of 5hmC in the one or more prostate cells is determined by high-resolution light microscopy in conjunction with computer-assisted image analysis after the one or more prostate cells have been subjected to immunofluorescence staining with an antibody specific for 5hmC.

7. The method of claim 1, wherein the quantity of AMACR in the one or more prostate cells is determined by high-resolution light microscopy in conjunction with computer-assisted image analysis after the one or more prostate cells have been subjected to immunofluorescence staining with an antibody specific for AMACR.

8. The method of claim 1, wherein the quantity of gDNA in the one or more prostate cells is determined by high-resolution light microscopy in conjunction with computer-assisted image analysis after the one or more prostate cells have been treated with 6-diamidino-2-phenylindole (DAPI).

9. The method of claim 8, wherein the microscope is a confocal scanning microscope with a resolution equal to or less than one micrometer.

10. The method of claim 1, wherein the cancer stage in the one or more cancerous prostate cells is stage I, stage II, stage III, or stage IV.

11. The method of claim 1, further comprising stratifying the human subject for monitoring or treatment based on the cancer grade (Gleason score) and the cancer stage associated with the one or more cancerous prostate cells.

12. The method of claim 11, wherein the treatment is radiation therapy, chemotherapy, or surgery, or combinations thereof.

13. The method of claim 12, wherein the surgery is prostatectomy.

14. The method of claim 12, wherein the surgery is partial prostatectomy.

15. The method of claim 12, wherein the surgery is radical prostatectomy.

* * * * *